United States Patent

Pan

[11] Patent Number: 6,013,257
[45] Date of Patent: Jan. 11, 2000

[54] NEUROTACTIN AND USES THEREFOR

[75] Inventor: Yang Pan, Brookline, Mass.

[73] Assignee: Millennium BioTherapeutics, Inc., Cambridge, Mass.

[21] Appl. No.: 08/991,426

[22] Filed: Dec. 16, 1997

Related U.S. Application Data

[63] Continuation-in-part of application No. 08/851,160, May 5, 1997, which is a continuation-in-part of application No. 08/643,798, May 7, 1996.

[51] Int. Cl.[7] ........................ A61K 39/395; A61K 39/00; C07K 16/24

[52] U.S. Cl. .................................... 424/139.1; 424/130.1; 424/152.1; 424/172.1; 424/810; 530/387.9; 530/868

[58] Field of Search .............................. 424/130.1, 152.1, 424/172.1, 139.1, 810; 530/387.9, 868

[56] References Cited

FOREIGN PATENT DOCUMENTS

WO 95/17092  6/1995  WIPO.
WO 95/32282  11/1995  WIPO.

OTHER PUBLICATIONS

Baggiolini et al., "CC chemokines in allergic inflammation" Immun. Today 15:(3)127–133, 1994.
Barthalay et al., "Drosophila neurotactin mediates heterophilic cell Adhesion" EMBO Journal 9:(11)3603–3609, 1990.
Burkly et al., "T–Cell tolerance by clonal anergy in transgenic mice with nonlymphoid expression: . . . " Nature 342:564–566, 1989.
Cocket et al., "The use of engineered E1A genes to transactivate the hCMV–MIE promoter in permanent CHO cell lines" Nucl. Acids Res. 19:319–325, 1991.
Kelner et al., "Lymphotactin: A cytokine that represents a new class of chemokine" Science 266:1395–1399, 1994.
Massague et al., "Membrane–Anchored Growth Factors" Annu. Rev. Biochem. 62:515–41, 1993.
Owens et al., "Inflammatory cytokines in the brain: does the CNS shape immune responses?" Immun. Today 15:(12)566–571, 1994.
Pan et al., "Neurotactin, a membrane–anchored chemokine upregulated in brain inflammation" Nature 387:611–617, 1997.
Rowland, L., "Blood–Brain Barrier, Cerbrospinal Fluid, Brain Edema, and Hydrocephalus" Appendix I, *Brain Fluids and Their Disorders*, pp. 837–844.
Santiago et al., "Characterization and gene cloning of neurotactin, a Drosophila transmembrane protein related to cholinesterases" EMBO Journal 9:3593–3601, 1990.
Brocke, S et al. Experimental autoimmune encephalomyelitis in the mouse. in: Autoimmune Disease Models: A Guidebook. Cohen and Miller, eds. Academic Press, San Diego, CA. pp. 1–14, 1994.
Swanborg, RH. Clin. Immunol. Immunopath. 77(1):4–13, Oct. 1995.

*Primary Examiner*—David Saunders
*Assistant Examiner*—F. Pierre VanderVegt
*Attorney, Agent, or Firm*—Fish & Richardson, P.C.

[57] ABSTRACT

The present invention relates to a method for the treatment of multiple sclerosis comprising administering to a patient an antibody which binds to neurotactin. Neurotactin is a membrane-anchored chemokine which is highly expressed in normal mammalian brain.

4 Claims, 8 Drawing Sheets

```
                                            M   A   P   S   P   L   A   W   L   L    10
GTCGACCCACGCGTCCGGCCGAATTCCTGCACTCCAGCC ATG GCT CCC TCG CCG CTC GCG TGG CTG CTG    69

R   L   A   A   F   F   H   L   C   T   L   L   P   G   Q   H   L   G   M   T    30
CGC CTG GCC GCG TTC TTC CAT TTG TGT ACT CTG CTG CCG GGT CAG CAC CTC GGC ATG ACG   129

K   C   E   I   M   C   D   K   M   T   S   R   I   P   V   A   L   L   I   R    50
AAA TGC GAA ATC ATG TGC GAC AAG ATG ACC TCA CGA ATC CCA GTG GCT TTG CTC ATC CGC   189

Y   Q   L   N   Q   E   S   C   G   K   R   A   I   V   L   E   T   T   Q   H    70
TAT CAG CTA AAC CAG GAG TCC TGC GGC AAG CGT GCC ATT GTC CTG GAG ACG ACA CAG CAC   249

R   R   F   C   A   D   P   K   E   K   W   V   Q   D   A   M   K   H   L   D    90
AGA CGC TTC TGT GCT GAC CCG AAG GAG AAA TGG GTC CAA GAC GCC ATG AAG CAT CTG GAT   309

H   Q   A   A   A   L   T   K   N   G   G   K   F   E   K   R   V   D   N   V   110
CAC CAG GCT GCT GCC CTC ACT AAA AAT GGT GGC AAG TTT GAG AAG CGG GTG GAC AAT GTG   369

T   P   G   I   T   L   A   T   R   G   L   S   P   S   A   L   T   K   P   E   130
ACA CCT GGG ATC ACC TTG GCC ACT AGG GGA CTG TCC CCA TCT GCC CTG ACA AAG CCT GAA   429

S   A   T   L   E   D   L   A   L   E   L   T   T   I   S   Q   E   A   R   G   150
TCC GCC ACA TTG GAA GAC CTT GCT TTG GAA CTG ACT ACT ATT TCC CAG GAG GCC AGG GGG   489

T   M   G   T   S   Q   E   P   P   A   A   V   T   G   S   S   L   S   T   S   170
ACC ATG GGG ACT TCC CAA GAG CCA CCG GCA GCA GTG ACC GGA TCA TCT CTC TCA ACT TCC   549

E   A   Q   D   A   G   L   T   A   K   P   Q   S   I   G   S   F   E   A   A   190
GAG GCA CAG GAT GCA GGG CTT ACG GCT AAG CCT CAG AGC ATT GGA AGT TTT GAG GCG GCT   609

D   I   S   T   T   V   W   P   S   P   A   V   Y   Q   S   G   S   S   S   W   210
GAC ATC TCC ACC ACC GTT TGG CCG AGT CCT GCT GTC TAC CAA TCT GGA TCT AGC TCC TGG   669

A   E   E   K   A   T   E   S   P   S   T   T   A   P   S   P   Q   V   S   T   230
GCT GAG GAA AAA GCT ACT GAG TCC CCC TCC ACT ACA GCC CCA TCT CCT CAG GTG TCC ACT   729

T   S   P   S   T   P   E   E   N   V   G   S   E   G   Q   P   P   W   V   Q   250
ACT TCA CCT TCA ACC CCA GAG GAA AAT GTT GGG TCC GAA GGC CAA CCC CCA TGG GTC CAG   789

G   Q   D   L   S   P   E   K   S   L   G   S   E   E   I   N   P   V   H   T   270
GGA CAG GAC CTC AGT CCA GAG AAG TCT CTA GGG TCT GAG GAG ATA AAC CCA GTT CAT ACT   849

D   N   F   Q   E   R   G   P   G   N   T   V   H   P   S   V   A   P   I   S   290
GAT AAT TTC CAG GAG AGG GGG CCT GGC AAC ACA GTC CAC CCC TCA GTG GCT CCC ATC TCC   909

S   E   E   T   P   S   P   E   L   V   A   S   G   S   Q   A   P   K   I   E   310
TCT GAA GAG ACC CCC AGC CCA GAG CTG GTG GCC TCG GGC AGC CAG GCT CCT AAG ATA GAG   969

E   P   I   H   A   T   A   D   P   Q   K   L   S   V   L   I   T   P   V   P   330
GAA CCC ATC CAT GCC ACT GCA GAT CCC CAG AAA CTG AGT GTG CTT ATC ACT CCT GTC CCC  1029

D   T   Q   A   A   T   R   R   Q   A   V   G   L   L   A   F   L   G   L   L   350
GAC ACC CAG GCA GCC ACA AGG AGG CAG GCA GTG GGG CTA CTG GCT TTC CTT GGT CTT CTT  1089
```

FIG. 1A

|   F   |   C   |   L   |   G   |   V   |   A   |   M   |   F   |   A   |   Y   |   Q   |   S   |   L   |   Q   |   G   |   C   |   P   |   R   |   K   |   M   | 370 |
|---|---|---|---|---|---|---|---|---|---|---|---|---|---|---|---|---|---|---|---|---|

TTC TGC CTA GGG GTG GCC ATG TTT GCT TAC CAG AGC CTT CAG GGC TGT CCC CGC AAA ATG 1149

```
  A   G   E   M   V   E   G   L   R   Y   V   P   R   S   C   G   S   N   S   Y  390
GCG GGG GAA ATG GTA GAA GGC CTC CGC TAC GTC CCC CGT AGC TGT GGC AGT AAC TCA TAC 1209

V   L   V   P   V   *                                                         395
GTC CTG GTG CCA GTG TGA                                                         1227
```

GCTGCTTGCCTGCCTGCCTGTGTCCAGAGTGTGATTCGGACAGCTGTCTGGGGACCCCCCCCCATCCTCATACCCACCT 1306

TCATCCACGCTGGGGAAATGGGAATGGAGAAGCTGGACCCTCCAGGGGCTGTGGGCTCCATCCAATCCCCCCTCCCCCG 1385

AGGGGTGGCCCCGGAGGCCACCCTAGACCACTATTCACTTATCAGAGACAGAGCAGGTGACCTTCCAGCTCCTCTATAT 1464

TTGAAAGAATCCTCTGCTGCTGGCTGGTTAGAGGGGCCCTTGACACCCCAACTCCAGTGAACAATTATTTATTGGATTC 1543

CCAGCCCCTGCGACGACACCTGTTTCCCGCGCGCACCGTGGTCCGCCCATATCACAAGCAGCAGGCCAGGCCTATCTGC 1622

CTGTCCCCCTGACCTCCTTGTGTCTCCTGGCTTTGCTGCAGTCGCCAGCCCTTCTCCTCCCCGGCCAGCTGCGGTGCTA 1701

TCTGCCCTATGTCTCCCTCTATCCCCTGTACAGAGCGCACCACCATCACCATCAAAAAAAAAAAAAAAAAAAAAGGGCGG 1780

CCGC 1784

FIG. 1B

```
AAGCTTGGCACGAGGGCACTGAGCTCTGCCGCCTGGCTCTAGCCGCCTGCCTGGCCCCGCCGGGACTCTTGCCCACCC    79
          M   A   P   I   S   L   S   W   L   L   R   L   A   T   F   C   H   L    18
TCAGCC ATG GCT CCG ATA TCT CTG TCG TGG CTG CTC CGC TTG GCC ACC TTC TGC CAT CTG    139
  T   V   L   L   A   G   Q   H   H   G   V   T   K   C   N   I   T   C   S   K    38
ACT GTC CTG CTG GCT GGA CAG CAC CAC GGT GTG ACG AAA TGC AAC ATC ACG TGC AGC AAG    199
  M   T   S   K   I   P   V   A   L   L   I   H   Y   Q   Q   N   Q   A   S   C    58
ATG ACA TCA AAG ATA CCT GTA GCT TTG CTC ATC CAC TAT CAA CAG AAC CAG GCA TCA TGC    259
  G   K   R   A   I   I   L   E   T   R   Q   H   R   L   F   C   A   D   P   K    78
GGC AAA CGC GCA ATC ATC TTG GAG ACG AGA CAG CAC AGG CTG TTC TGT GCC GAC CCG AAG    319
  E   Q   W   V   K   D   A   M   Q   H   L   D   R   Q   A   A   A   L   T   R    98
GAG CAA TGG GTC AAG GAC GCG ATG CAG CAT CTG GAC CGC CAG GCT GCT GCC CTA ACT CGA    379
  N   G   G   T   F   E   K   Q   I   G   E   V   K   P   R   T   T   P   A   A    118
AAT GGC GGC ACC TTC GAG AAG CAG ATC GGC GAG GTG AAG CCC AGG ACC ACC CCT GCC GCC    439
  G   G   M   D   E   S   V   V   L   E   P   E   A   T   G   E   S   S   S   L    138
GGG GGA ATG GAC GAG TCT GTG GTC CTG GAG CCC GAA GCC ACA GGC GAA AGC AGT AGC CTG    499
  E   P   T   P   S   S   Q   E   A   Q   R   A   L   G   T   S   P   E   L   P    158
GAG CCG ACT CCT TCT TCC CAG GAA GCA CAG AGG GCC CTG GGG ACC TCC CCA GAG CTG CCG    559
  T   G   V   T   G   S   S   G   T   R   L   P   P   T   P   K   A   Q   D   G    178
ACG GGC GTG ACT GGT TCC TCA GGG ACC AGG CTC CCC CCG ACG CCA AAG GCT CAG GAT GGA    619
  G   P   V   G   T   E   L   F   R   V   P   P   V   S   T   A   A   T   W   Q    198
GGG CCT GTG GGC ACG GAG CTT TTC CGA GTG CCT CCC GTC TCC ACT GCC GCC ACG TGG CAG    679
  S   S   A   P   H   Q   P   G   P   S   L   W   A   E   A   K   T   S   E   A    218
AGT TCT GCT CCC CAC CAA CCT GGG CCC AGC CTC TGG GCT GAG GCA AAG ACC TCT GAG GCC    739
  P   S   T   Q   D   P   S   T   Q   A   S   T   A   S   S   P   A   P   E   E    238
CCG TCC ACC CAG GAC CCC TCC ACC CAG GCC TCC ACT GCG TCC TCC CCA GCC CCA GAG GAG    799
  N   A   P   S   E   G   Q   R   V   W   G   Q   G   Q   S   P   R   P   E   N    258
AAT GCT CCG TCT GAA GGC CAG CGT GTG TGG GGT CAG GGA CAG AGC CCC AGG CCA GAG AAC    859
  S   L   E   R   E   E   M   G   P   V   P   A   H   T   D   A   F   Q   D   W    278
TCT CTG GAG CGG GAG GAG ATG GGT CCC GTG CCA GCG CAC ACG GAT GCC TTC CAG GAC TGG    919
  G   P   G   S   M   A   H   V   S   V   V   P   V   S   E   G   T   P   S    298
GGG CCT GGC AGC ATG GCC CAC GTC TCT GTG GTC CCT GTC TCC TCA GAA GGG ACC CCC AGC    979
  R   E   P   V   A   S   G   S   W   T   P   K   A   E   E   P   I   H   A   T    318
AGG GAG CCA GTG GCT TCA GGC AGC TGG ACC CCT AAG GCT GAG GAA CCC ATC CAT GCC ACC    1039
```

FIG. 2A

```
M   D   P   Q   R   L   G   V   L   I   T   P   V   P   D   A   Q   A   A   T   338
ATG GAC CCC CAG AGG CTG GGC GTC CTT ATC ACT CCT GTC CCT GAC GCC CAG GCT GCC ACC 1099

R   R   Q   A   V   G   L   L   A   F   L   G   L   L   F   C   L   G   V   A   358
CGG AGG CAG GCG GTG GGG CTG CTG GCC TTC CTT GGC CTC CTC TTC TGC CTG GGG GTG GCC 1159

M   F   T   Y   Q   S   L   Q   G   C   P   R   K   M   A   G   E   M   A   E   378
ATG TTC ACC TAC CAG AGC CTC CAG GGC TGC CCT CGA AAG ATG GCA GGA GAG ATG GCG GAG 1219

G   L   R   Y   I   P   R   S   C   G   S   N   S   Y   V   L   V   P   V   *   397
GGC CTT CGC TAC ATC CCC CGG AGC TGT GGT AGT AAT TCA TAT GTC CTG GTG CCC GTG TGA 1279

ACTCCTCTGGCCTGTGTCTAGTTGTTTGATTCAGACAGCTGCCTGGGATCCCTCATCCTCATACCCACCCCCACCCAAG 1358

GGCCTGGCCTGAGCTGGGATGATTGGAGGGGGGAGGTGGGATCCTCCAGGTGCACAAGCTCCAAGCTCCCAGGCATTCC 1437

CCAGGAGGCCAGCCTTGACCATTCTCCACCTTCCAGGGACAGAGGGGGTGGCCTCCCAACTCACCCCAGCCCCAAAACT 1516

CTCCTCTGCTGCTGGCTGGTTAGAGGTTCCCTTTGACGCCATCCCAGCCCCAATGAACAATTATTTATTAAATGCCCAG 1595

CCCCTTCTGAAAAAAAAAAAAAAAAAAAAAAAAAAAAAAAAAAAAAATTCCTGCGGCCGC                    1654
```

FIG. 2B

```
  1 MAPISLSWLLRLATFCHLTVLLAGQHHGVTKCNITCSKMTSKIPVALLIH  50
    ||| .|.||||||.| ||..||:||| |:|||:| |.||||:||||||||:
  1 MAPSPLAWLLRLAAFFHLCTLLPGQHLGMTKCEIMCDKMTSRIPVALLIR  50

51 YQQNQASCGKRAIILETRQHRLFCADPKEQWVKDAMQHLDRQAAALTRNG 100
    || ||.||||||||:||| ||| |||||||.||.|||.|||:|||||:||
 51 YQLNQESCGKRAIVLETTQHRRFCADPKEKWVQDAMKHLDHQAAALTKNG 100

101 GTFEKQIGEVKPRTTPAAGGMDESVVLEPE.ATGESSSLEPTPSSQEAQR 149
    |.|||.:::|.| .| |. |:..|.: .|| ||| |. .||  |.  ||||.
101 GKFEKRVDNVTPGITLATRGLSPSALTKPESATLEDLALELTTISQEARG 150

150 ALGTSPELPTGVTGSSGTRLPPTPKAQDGG....PVGTELFRVPPVSTAA 195
    .:||||.| |.:||||||   .|..|||:|    |  |:.: | .:.:|| .
151 TMGTSQEPPAAVTGSS....LSTSEAQDAGLTAKPQSIGSFEAADIST.T 195

196 TWQSSAPHQPGPSLWAEAKTSEAPSTQDPSTQASTASSPAPEENAPSEGQ 245
    .|.|.|..|.|.| |||.|..|.||| .||.|.||.|...||||..||||
196 VWPSPAVYQSGSSSWAEEKATESPSTTAPSPQVSTTSPSTPEENVGSEGQ 245

246 RVWGQGQSPRPENSLEREEMGPVPAHTDAFQDWGPGSMAHVSVVPVSSEG 295
    ..|.|||. .||.||:.||:.|| |||.||::|||. .|.||.|:|||:
246 PPWVQGQDLSPEKSLGSEEINPV..HTDNFQERGPGNTVHPSVAPISSEE 293

296 TPSREPVASGSWTPKAEEPIHATMDPQRLGVLITPVPDAQAATRRQAVGL 345
    |||.| ||||| .|| ||||||||| |||:|:|||||||||.||||||||||
294 TPSPELVASGSQAPKIEEPIHATADPQKLSVLITPVPDTQAATRRQAVGL 343

346 LAFLGLLFCLGVAMFTYQSLQGCPRKMAGEMAEGLRYIPRSCGSNSYVLV 395
    ||||||||||||||.|||||||||||||||.||||:|||||||||||||||
344 LAFLGLLFCLGVAMFAYQSLQGCPRKMAGEMVEGLRYVPRSCGSNSYVLV 393

NEUROTACTIN AND USES THEREFOR

This application is a continuation-in-part of U.S. Ser. No. 08/851,160, filed May 5, 1997, which is a continuation-in-part of U.S. Ser. No. 08/643,798 filed May 7, 1996.

BACKGROUND OF THE INVENTION

This invention relates to a new chemokine, neurotactin, and methods of preparing and using neurotactin.

Chemokines are proteins involved in the activation and chemotaxis of leukocytes. They are believed to be important mediators of inflammation (Baggiolini et al., *Immunology Today* 15:127, 1994).

Chemokines have been divided into three families. In chemokines of the C-X-C family, one amino acid separates the first two cysteines. Chemokines in this family are thought to be involved in the chemotaxis of neutrophils, induction of changes in cell shape, transient increase of intracellular calcium, granule exocytosis, and respiratory burst. Interleukin-8 (IL-8), neutrophil activating protein-2 (NAP-2) and granulocyte chemotactic protein (GCP) belong to this class. All known C-X-C chemokines have been mapped to human chromosome 4 and mouse chromosome 5.

In the C—C family, the first two cysteines are adjacent to one another. Members of this family are chemotactic for monocytes, but not neutrophils. Recent studies have shown that they are capable of activating basophils and eosinophils. Proteins belonging to the C—C class of chemokines include monocyte chemotactic proteins 1, 2, and 3 (MCP-1, MCP-2, and MCP-3), RANTES, and macrophage inflammatory proteins α and β (MIP-1α and MIP-1β). Recently, MIP-3, MIP-4, and MIP-1γ have also been described (WO 95/17092). All known C—C chemokines have been mapped to human chromosome 17 and mouse chromosome 11.

An example of a third class of chemokine has also been identified. This chemokine, lymphotactin, was isolated from progenitor T lymphocytes. Lymphotactin is chemotactic to lymphocytes (Kelner et al., *Science* 266:1395, 1994). Unlike the chemokines of the C—C and C-X-C families in which two disulfide bonds stabilize the protein, lymphotactin has only one disulfide bond. Lymphotactin was mapped to human and mouse chromosome 1.

A variety of cell types are involved in the various inflammatory states. For example, acute infiltrates found after bacterial infection are mainly neutrophilic, while mononuclear cells predominate after infection by an intracellular pathogen. Basophils and eosinophils dominate in both immediate-type allergic response and autoimmune diseases. Increased understanding of the regulation of these various cell types by chemokines will facilitate the development of more effective therapies for disorders related to inflammation.

Brain inflammation is only partially understood. It appears that the brain regulates its own immune response rather than being an immunological privileged organ (Trevor et al., *Immunology Today* 15:566, 1994). Inflammatory cytokine production in the brain is initiated by infiltrating T cells but longer term inflammation is dependent on CNS resident cells, such as microglial cells.

SUMMARY OF THE INVENTION

The present invention relates to the identification and characterization of neurotactin, a novel membrane-anchored chemokine. Sequence analysis of neurotactin reveals that, while it includes an amino terminal domain which resembles that of other chemokines, it has an overall structure which distinguishes it from all presently identified chemokines.

The expression pattern of neurotactin is unusual for a chemokine in that it is highly expressed in normal mammalian brain. Similar to other chemokines, neurotactin is upregulated in bone marrow stromal cells, endothelial cells, and fibroblasts which have been treated with lipopolysaccharide (LPS) and phorbal myristate acid (PMA), both of which are activators.

A murine form of neurotactin described herein encodes a protein of 395 amino acids (FIGS. 1A–1B). This murine form of the protein (SEQ ID NO:2) begins with an approximately 21 amino acid long signal sequence followed by an apparent extracellular domain of approximately 318 amino acids extending from about amino acid 22 to about amino acid 339; a transmembrane domain of approximately 21 amino acids extending from about amino acid 340 to about amino acid 360; and a cytoplasmic domain of approximately 35 amino acids extending from about amino acid 361 to amino acid 395.

A human form of neurotactin described herein encodes a protein of 397 amino acids (FIGS. 2A–2B). This human form of the protein (SEQ ID NO:4) begins with an approximately 21 amino acid long signal sequence followed by an apparent extracellular domain of approximately 321 amino acids extending from about amino acid 22 to about amino acid 341; a transmembrane domain of approximately 22 amino acids extending from about amino acid 342 to about amino acid 362; and a cytoplasmic domain of approximately 35 amino acids extending from about amino acid 363 to amino acid 397.

Within the extracellular domain of both the murine form of neurotactin described herein and the human form of neurotactin described herein is a chemokine-like domain which extends from about amino acid 22 to about amino acid 92.

Overall, the human form of neurotactin described herein is 67% identical at the amino acid level to the murine form of neurotactin described herein. The highest homology between the two forms is found in transmembrane and cytoplasmic domains, suggesting that both domains have important functional roles. High homology between the two forms is also found in the chemokine-like amino terminal region.

The invention features an isolated nucleic acid which encodes a neurotactin polypeptide. The nucleic acid can have the nucleotide sequence of, e.g., FIGS. 1A–1B, SEQ ID NO:1 (murine), or FIGS. 2A–2B, SEQ ID NO:3 (human). Preferably, the neurotactin polypeptide includes an amino acid sequence substantially identical to the amino acid sequence shown in FIGS. 1A–1B (SEQ ID NO:2) or the amino acid sequence shown in FIGS. 2A–2B (SEQ ID NO:4). Also considered within the scope of the invention are isolated nucleic acids that hybridize under stringent conditions to nucleic acids having the nucleotide sequence of, e.g., FIGS. 1A–1B, SEQ ID NO:1 (murine), or FIGS. 2A–2B, SEQ ID NO:3 (human). Substantially pure polypeptides encoded by nucleic acids that hybridize under stringent conditions to, e.g., SEQ ID NO:1 or SEQ ID NO:3, are also featured in the invention.

Preferred neurotactin polypeptides have a sequence which is substantially identical to that of a naturally occurring neurotactin polypeptide, e.g., the mature form of human neurotactin described herein.

By "isolated nucleic acid" is meant DNA that is not immediately contiguous with both of the coding sequences with which it is immediately contiguous (one on the 5' end and one on the 3' end) in the naturally occurring genome of the organism from which it is derived. Thus, a recombinant nucleic acid could include some or all of the 5' non-coding (e.,g., promoter) sequences which are immediately contiguous to the coding sequence. The term therefore includes, for example, a recombinant DNA which is incorporated into a vector; into an autonomously replicating plasmid or virus, such as a retrovirus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By "mature human neurotactin" is meant a polypeptide having the sequence shown in FIGS. 2A–2B (SEQ ID NO:4) from about amino acid 22 to amino acid 397. Polypeptides substantially identical to mature human neurotactin have an amino acid sequence which is at least 85%, preferably 90%, and most preferably 95% or even 99% identical to the amino acid sequence of the neurotactin polypeptide of FIGS. 2A–2B (SEQ ID NO:4)

By "substantially identical" is meant a polypeptide or nucleic acid having a sequence that is at least 85%, preferably 90%, and more preferably 95% or more identical to the sequence of the reference amino acid or nucleic acid sequence. For polypeptides, the length of the reference polypeptide sequence will generally be at least 16 amino acids, preferably at least 20 amino acids, more preferably at least 25 amino acids, and most preferably 35 amino acids. For nucleic acids, the length of the reference nucleic acid sequence will generally be at least 50 nucleotides, preferably at least 60 nucleotides, more preferably at least 75 nucleotides, and most preferably 110 nucleotides.

Sequence identity can be measured using sequence analysis software (e.g., Sequence Analysis Software Package of the Genetics Computer Group, University of Wisconsin Biotechnology Center, 1710 University Avenue, Madison, Wis. 53705), with the default parameters therein.

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. of course, many other polypeptides will meet the same criteria.

Polypeptides corresponding to one or more domains of neurotactin, e.g., the extracellular domain or the chemokine-like domain (about amino acid 22 to about amino acid 92 of a form of neurotactin described herein), are also within the scope of the invention. Preferred polypeptides are those which are soluble under normal physiological conditions. Also within the invention are soluble fusion proteins in which a full-length form of neurotactin or a portion (e.g., one or more domains) thereof is fused to an unrelated protein or polypeptide (i.e., a fusion partner) to create a fusion protein.

The invention also features isolated nucleic acid sequences that encode a portion of neurotactin, including but not limited to the extracellular domain, the transmembrane domain, the cytoplasmic domain, the chemokine-like domain, and various functional domains of neurotactin. Also within the invention are nucleic acids encoding polypeptides corresponding to one or more domains of neurotactin, e.g., the extracellular domain or the chemokine-like domain. Preferred nucleic acids encode polypeptides that are soluble under normal physiological conditions. Also within the invention are nucleic acids encoding fusion proteins in which a portion of neurotactin or a portion (e.g., one or more domains) thereof is fused to an unrelated protein or polypeptide (i.e., a fusion partner) to create a fusion protein.

Encompassed within the invention are nucleic acid sequences that encode forms of neurotactin in which sequences are altered or deleted.

The nucleic acids of the invention include nucleic acids encoding mature neurotactin as well as neurotactin polypeptides fused to a polypeptide which facilitates secretion, e.g., a secretory sequence. Such a fused protein is typically referred to as a preprotein. The secretory sequence can be removed by the host cell to form the mature protein. Also within the invention are nucleic acids that encode mature neurotactin fused to a polypeptide sequence to produce an inactive proprotein. Proproteins can be converted into the active form of the protein by removal of the inactivating sequence.

The invention also encompasses nucleic acids that hybridize under stringent conditions to a nucleic acid encoding a neurotactin polypeptide. "Stringent conditions" means hybridization at 50° C. in Church buffer (7% SDS, 0.5% $NaHPO_4$, 1 mM EDTA, 1% BSA) and washing at 50° C. in 2× SSC. The hybridizing portion of the hybridizing nucleic acids are preferably 20, 30, 50, or 70 bases long. Preferably, the hybridizing portion of the hybridizing nucleic acid is 95% or even 98% identical to the sequence of a portion of a nucleic acid encoding a neurotactin polypeptide. Hybridizing nucleic acids of the type described above can be used as a cloning probe, a primer (e.g., a PCR primer), or a diagnostic probe. Preferred hybridizing nucleic acids encode a polypeptide having some or all of the biological activities possessed by naturally-occurring neurotactin. Hybridizing nucleic acids can be splice variants encoded by one of the neurotactin genes described herein. Thus, they may encode a protein which is shorter or longer than the various forms of neurotactin described herein. Hybridizing nucleic acids may also encode proteins which are related to neurotactin (e.g, proteins encoded by genes which include a portion having a relatively high degree of identity to a neurotactin gene described herein).

The invention also features substantially pure neurotactin polypeptides. Among the polypeptides encompassed within the invention are those corresponding to the extracellular domain, the transmembrane domain, the cytoplasmic domain, and various functional domains of neurotactin including the chemokine-like domain which corresponds to a domain extending from about amino acid 22 to about amino acid 92 of the form of murine neurotactin described herein and to a domain extending from about amino acid 22 to about amino acid 92 of the form of human neurotactin described herein.

The invention also encompasses polypeptides and nucleic acids whose sequences are substantially identical to that of a form of neurotactin described herein.

By "protein" and "polypeptide" is meant any chain of amino acids, regardless of length or post-translational modification (e.g., glycosylation or phosphorylation).

By "substantially pure" is meant a preparation which is at least 60% by weight (dry weight) the compound of interest, i.e., a neurotactin polypeptide. Preferably the preparation is at least 75%, more preferably at least 90%, and most preferably at least 99%, by weight the compound of interest. Purity can be measured by any appropriate standard method, e.g., column chromatography, polyacrylamide gel electrophoresis, or HPLC analysis.

The term "nucleic acid" encompasses both RNA and DNA, including cDNA, genomic DNA, and synthetic (e.g., chemically synthesized) DNA. The nucleic acid may be double-stranded or single-stranded. Where single-stranded, the nucleic acid may be the sense strand or the antisense strand.

The polypeptides of the invention include, but are not limited to: recombinant polypeptides, natural polypeptides, and synthetic polypeptides as well as polypeptides which are preproteins or proproteins.

The polypeptides of the invention can be expressed fused to another polypeptide, e.g., a marker polypeptide or fusion partner. For example, the polypeptide can be fused to a hexa-histidine tag to facilitate purification of bacterially expressed protein or a hemagglutinin tag to facilitate purification of protein expressed in eukaryotic cells.

The invention features transformed cells harboring a nucleic acid encompassed by the invention. The invention also features vectors which include a nucleic acid of the invention which is properly positioned for expression. For example, the vector can be an expression vector, and can include one or more regulatory elements. Regulatory elements that can influence the expression of the nucleic acid inserted into the vector, such as regulatory elements that direct tissue-specific expression, are well known to those of skill in the art. Examples of regulatory elements include the cytomegalovirus hCMV immediate early gene, the early promoter of SV40 adenovirus, the late promoter of SV40 adenovirus, the lac system, the trp system, the TAC system, the TRC system, the major operator and promoter regions of phage lambda, the control regions of fd coat protein, the promoter for 3-phosphoglycerate kinase, the promoters of acid phosphatase, and the promoters of the yeast α-mating factors. The vector can be a plasmid, or a virus, such as a retrovirus.

By "transformed cell" is meant a cell into which (or into an ancestor of which) has been introduced, by means of recombinant DNA techniques, a DNA molecule encoding (as used herein) neurotactin polypeptide.

By "positioned for expression" is meant that the selected DNA molecule is positioned adjacent to one or more sequence elements which direct transcription and/or translation of the sequence such that the sequence elements can control transcription and/or translation of the selected DNA (i.e., the selected DNA is operably associated with the sequence elements). Such operably associated elements can be used to facilitate the production of a neurotactin polypeptide.

The invention also features purified antibodies which specifically bind a neurotactin protein or polypeptide.

By "purified antibody" is meant an antibody which is at least 60%, by dry weight, free from the proteins and naturally-occurring organic molecules with which it is naturally associated. Preferably, the preparation is at least 75%, more preferably at least 90%, and most preferably at least 99%, by dry weight, antibody.

By "specifically binds" is meant an antibody that recognizes and binds to a particular antigen, e.g., neurotactin polypeptide, but which does not substantially recognize and bind to other molecules in a sample, e.g., a biological sample, which naturally includes neurotactin.

The invention also features antagonists and agonists of neurotactin. Antagonists can inhibit one or more of the functions of neurotactin. Suitable antagonists can include large or small molecules, antibodies to neurotactin, and neurotactin polypeptides which compete with a native form of neurotactin. Agonists of neurotactin will enhance or facilitate one or more of the functions of neurotactin. Suitable agonists can include, for example, large or small molecules and antibodies to neurotactin.

Also within the invention are nucleic acid molecules which can be used to interfere with neurotactin expression, e.g., antisense molecules and ribozymes.

The invention features substantially pure neurotactin polypeptides. In various preferred embodiments the polypeptide is soluble, the polypeptide includes the chemokine-like domain of neurotactin, the polypeptide includes the extracellular domain of neurotactin, the polypeptide is at least 80% identical to the amino acid sequence from amino acid 22 to amino acid 92 in SEQ ID NO:4, the polypeptide is at least 90% identical to the amino acid sequence from amino acid 22 to amino acid 92 in SEQ ID NO:4, the polypeptide has an amino acid sequence identical to the amino acid sequence from amino acid 22 to amino acid 92 in SEQ ID NO:4, the polypeptide is at least 80% identical to the amino acid sequence from amino acid 22 to amino acid 397 in SEQ ID NO:4, the polypeptide is at least 90% identical to the amino acid sequence from amino acid 22 to amino acid 397 in SEQ ID NO:4, and the polypeptide has an amino acid sequence identical to the amino acid sequence from amino acid 22 to amino acid 397 in SEQ ID NO:4.

The invention also features a substantially pure polypeptide which includes a first portion and a second portion; the first portion includes a neurotactin polypeptide and the second portion includes an immunoglobulin constant region.

The invention also features a substantially pure polypeptide which includes a first portion and a second portion; the first portion includes a neurotactin polypeptide the second portion includes a detectable marker. Examples of detectable markers include β-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), β-galactosidase, and xanthine guanine phosphoribosyl-transferase (XGPRT).

In another aspect the invention features a recombinant nucleic acid encoding a neurotactin polypeptide. In various preferred embodiments the nucleic acid encodes a soluble neurotactin polypeptide, the nucleic acid encodes the chemokine-like domain of neurotactin, and the nucleic acid encodes the extracellular domain of neurotactin.

The invention also features a nucleic acid encoding a hybrid polypeptide. This hybrid polypeptide includes a first portion and a second portion; the first portion includes a neurotactin polypeptide; the second portion comprising an immunoglobulin constant region.

The invention also features a cell which harbors a recombinant nucleic acid encoding a neurotactin polypeptide; a vector which includes a nucleic acid encoding a neurotactin polypeptide.

In another aspect, the invention features an antibody which selectively binds to a neurotactin polypeptide. In a preferred embodiment, the antibody is a monoclonal antibody.

The invention also features a pharmaceutical composition which includes a neurotactin polypeptide.

The invention features a method for detecting inflammation. This method includes: (a) obtaining a biological sample; (b) contacting the sample with an antibody which selectively binds a neurotactin polypeptide; and (c) determining the amount of the antibody selectively bound to said biological sample as a measure of inflammation.

In another aspect, the invention features a method for treating inflammation in a patient which includes administering to the patient an inhibitor of neurotactin. Preferably, the inhibitor is an antibody which selectively binds to neurotactin.

The invention also features a method for inhibiting proliferation of progenitor cells in a patient. The method includes administering to the patient a substantially pure neurotactin polypeptide capable of inhibiting progenitor cell proliferation. The invention also includes a method of suppressing proliferation of an actively dividing myeloid cell. This method includes contacting the cell with an effective amount of a neurotactin polypeptide that is capable of inhibiting proliferation of myeloid cells.

The invention also features an adjunctive method for use with chemotherapy or radiation therapy in a patient. The method includes: administering an effective amount of a neurotactin polypeptide to the patient, and administering chemotherapy or radiation therapy to the patient in conjunction with administration of the neurotactin polypeptide. By "adjunctive method" means administration before, during, or after chemotherapy or radiation therapy.

The invention also features a method of treating a hyperproliferative myeloid disease in a patient. The method includes administering to the patient an effective amount of a neurotactin polypeptide. In preferred embodiments, the disease is chronic myelogenous leukemia, polycythemia vera, and a hypermegakaryocytopoietic disorder.

The invention features a substantially pure protein which functionally interacts with neurotactin and a nucleic acid encoding a protein which functionally interacts with neurotactin.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed descriptions, and from the claims.

BRIEF DESCRIPTION OF THE DRAWINGS

FIGS. 1A–1B is a depiction of the nucleotide (SEQ ID NO:1) and amino acid (SEQ ID NO:2) sequences of a form of murine neurotactin, including a putative signal sequence. The unique arrangement between the C32 and C36 is underlined. Also underlined are R337 and R338, a potential enzyme cleavage site, and a potential membrane spanning domain from A340 to Y360.

FIGS. 2A–2B is a representation of the nucleotide (SEQ ID NO:3) and amino acid (SEQ ID NO:4) sequence of a form of human neurotactin, including a putative signal sequence. The unique arrangement between the C32 and C36 is underlined. Also underlined are the conserved R339 and R340, a potential enzyme cleavage site, and a potential membrane spanning domain from A342 to Y362.

FIG. 3 is a representation of the sequence alignment of full-length human (SEQ ID NO:4) and mouse (SEQ ID NO:2) neurotactin. In this representation, a vertical line between the two aligned sequences indicates an exact match, a single dot between the two aligned sequences indicates a conservative substitution, a pair of dots between the two aligned sequences indicates a very conservative substitution, and a series of dots within a sequence indicates a gap introduced to maximize alignment.

DETAILED DESCRIPTION

Neurotactin, described for the first time herein, is a novel chemokine that plays a role in inflammation, particularly inflammation of the brain.

Neurotactin mediates chemotaxis of specific cell types and is likely to induce release of inflammatory mediators. As a consequence, neurotactin may enhance leukocyte infiltration through the endothelial cell wall and have effect on microglial cells. Neurotactin, like certain other proteins, may have a functional secreted form as well as a functional membrane-bound form.

While it is clear that neurotactin is a chemokine, it is also clear that neurotactin is an example of a novel class of chemokines.

First, neurotactin has three spacer amino acids between the first two cysteines (CXXXC), compared with none or one in the CC or CXC chemokines, respectively.

Second, neurotactin has an unusual expression pattern. As with other chemokines, neurotactin can be upregulated in bone marrow stromal cells, endothelial cells, and fibroblasts when treated with LPS and PMA. However, unlike other chemokines, neurotactin is highly expressed in normal brain, which suggests involvement in brain function.

Third, the length of the predicted neurotactin protein, 395 amino acids for the murine form described herein and 397 amino acids for the human form described herein, is considerably longer than the majority of known chemokines. Further, the portions of murine and human neurotactin after the first 92 amino acids of the mature protein do not bear significant resemblance to any presently known, sequenced protein. The first 92 acids of both the murine and human forms of neurotactin described herein have greater than 40% identity to murine MCP-1 and human MCP-1, respectively.

Fourth, the neurotactin gene maps to a different chromosomal location than the three known classes of mouse chemokines. It is located on human chromosome 16 and mouse chromosome 8. The murine CC, CXC, and lymphotactin chemokines have been mapped to chromosomes 11, 5, and 1 respectively.

Taken together, these facts demonstrate that neurotactin represents a new class of chemokine, referred to herein as the δ class.

Figure 4:
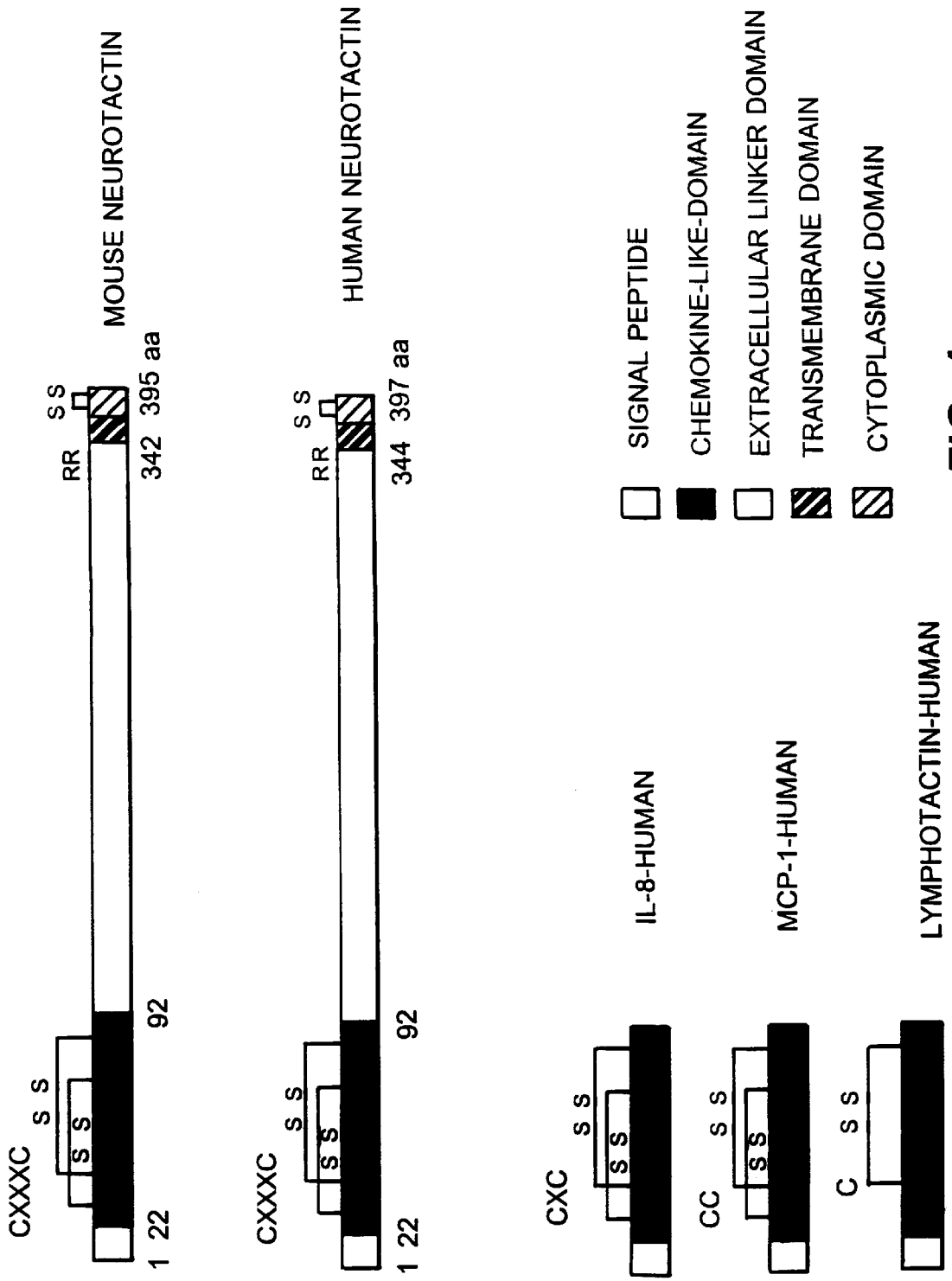
FIG. 4 is a comparison of the primary structure of neurotactin to that of known chemokine subfamilies.

FIG. 4 shows the primary structure of the murine and human forms of neurotactin, as well as the primary structures of human IL-8, human MCP-1, and human lymphotactin. Also shown in this figure are comparisons between the proteins. As can be seen from this figure, the primary structure of the first 92 amino acids of all five proteins are similar, whereas the two forms of neurotactin include an extracellular linker domain, a transmembrane domain, and a cytoplasmic domain not found in the other chemokines. The extracellular linker domain is the domain between the chemotactin-like domain and the transmembrane domain. The extracellular domain extends from about amino acid 93 to about amino acid 341 of the human form of neurotactin described herein and from about amino acid 93 to about amino acid 339 or the murine form of neurotactin described herein.

The two neighboring arginines adjacent the transmembrane region (amino acids 339 and 340 in the human form; amino acids 337 and 338 in the murine form) provide for the possibility of processing these proteins with proteolytic enzymes to detach them from the cell membrane.

Neurotactin Proteins and Polypeptides

Neurotactin proteins and polypeptides and neurotactin fusion proteins can be prepared for a wide range of uses including, but not limited to, generation of antibodies, preparation of reagents for diagnostic assays, identification of other molecules involved in inflammation (particularly brain inflammation), preparation of reagents for use in screening assays for inflammatory modulators, and preparation of therapeutic agents for treatment of inflammation-related disorders.

FIGS. 1A–1B shows the amino acid sequence of a form of murine neurotactin (SEQ ID NO:2). The domain from amino acid 1 to approximately amino acid 21 (in italics) forms a putative signal sequence. This putative signal sequence is followed by an apparent extracellular domain of approximately 318 amino acids extending from about amino acid 22 to about amino acid 339; a transmembrane domain of approximately 21 amino acids extending from about amino acid 340 to about amino acid 360; and a cytoplasmic domain of approximately 35 amino acids extending from about amino acid 361 to amino acid 395.

FIGS. 2A–2B shows the amino acid sequence of a form of human neurotactin (SEQ ID NO: 4). The domain from amino acid 1 to approximately amino acid 21 (in italics) forms a putative signal sequence. This putative signal sequence is followed by an apparent extracellular domain of approximately 321 amino acids extending from about amino acid 22 to about amino acid 341; a transmembrane domain of approximately 22 amino acids extending from about amino acid 342 to about amino acid 362; and a cytoplasmic domain of approximately 35 amino acids extending from about amino acid 363 to amino acid 397.

The invention encompasses, but is not limited to, neurotactin proteins and polypeptides that are functionally related to neurotactin encoded by the nucleotide sequence of FIGS. 1A–1B (murine, SEQ ID NO:1) or FIGS. 2A–2B (human, SEQ ID NO:3). Functionally related proteins and polypeptides include any protein or polypeptide sharing a functional characteristic with neurotactin, e.g., the ability to affect proliferation, differentiation, survival, apoptosis, or activation of a cell type whose proliferation, differentiation, survival, apoptosis, or activation is affected by neurotactin. Such functionally related neurotactin polypeptides include, but are not limited to, additions or substitutions of amino acid residues within the amino acid sequence encoded by the neurotactin sequences described herein which result in a silent change, thus producing a functionally equivalent gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to neurotactin DNA (using random mutagenesis techniques well known to those skilled in the art) and the resulting mutant neurotactin proteins can be tested for activity, site-directed mutations of the neurotactin coding sequence can be engineered (using site-directed mutagenesis techniques well known to those skilled in the art) to generate mutant neurotactins with increased function, e.g., greater stimulation of cell proliferation, or decreased function, e.g., lesser stimulation of cell proliferation.

To design functionally related and functionally variant neurotactin polypeptides, it is useful to distinguish between conserved positions and variable positions. FIG. 4 shows an alignment between the amino acid sequence of human neurotactin and murine neurotactin, which can be used to determine the conserved and variable amino acid positions.

To preserve neurotactin function, it is preferable that conserved residues are not altered. Moreover, alteration of non-conserved residues are preferably conservative alterations, e.g., a basic amino acid is replaced by a different basic amino acid. To produce altered function variants, it is preferable to make non-conservative changes at variable and/or conserved positions. Deletions at conserved and variable positions can also be used to create altered function variants.

Other mutations to the neurotactin coding sequence can be made to generate neurotactins that are better suited for expression, scale up, etc. in a selected host cell. For example, N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur (in N-X-S or N-X-T), and/or an amino acid deletion at the second position of any one or more of such recognition sequences, will prevent glycosylation at the modified tripeptide sequence. (See, e.g., Miyajima et al., *EMBO J.* 5:1193, 1986).

Preferred neurotactin polypeptides are those neurotactin polypeptides, or variants thereof, which stimulate chemotaxis of neutrophils. In determining whether a particular neurotactin polypeptide or variant thereof stimulates chemotaxis of neutrophils, one can use any standard neutrophil chemotaxis assay. One preferred assay is the chemotaxis assay described herein. Preferred neurotactin polypeptides and variants have 20%, 40%, 50%, 75%, 80%, or even 90% of the activity of the full-length, mature human form of neurotactin described herein. Such comparisons are generally based on equal concentrations of the molecules being compared. The comparison can also be based on the amount of protein or polypeptide required to reach 50% of the maximal stimulation obtainable.

Polypeptides corresponding to one or more domains of neurotactin, e.g., the extracellular domain and the chemokine-like domain, are also within the scope of the invention. Preferred polypeptides are those which are soluble under normal physiological conditions. Also within the invention are fusion proteins in which a portion (e.g., one or more domains) of neurotactin is fused to an unrelated protein or polypeptide (i.e., a fusion partner) to create a fusion protein. The fusion partner can be a moiety selected to facilitate purification, detection, or solubilization, or to provide some other function. Fusion proteins are generally produced by expressing a hybrid gene in which a nucleotide sequence encoding all or a portion of neurotactin is joined in-frame to a nucleotide sequence encoding the fusion partner. Fusion partners include, but are not limited to, the constant region of an immunoglobulin (IgFc). A fusion protein in which a neurotactin polypeptide is fused to IgFc can be more stable and have a longer half-life in the body than the neurotactin polypeptide on its own.

Also within the scope of the invention are various soluble forms of neurotactin. For example, the entire extracellular domain of neurotactin or a portion thereof can be expressed on its own or fused to a solubilization partner, e.g., an immunoglobulin.

The invention also features neurotactin polypeptides that can inhibit proliferation of progenitor cells. Such polypeptides are can be used to protect progenitor cells from the effects of chemotherapy and/or radiation therapy. Any convenient in vitro or in vivo assay can be used to determine whether a selected neurotactin polypeptide or variant thereof inhibits progenitor cell proliferation and is thus likely to be a suitable chemoprotective agent. Suitable in vitro assays include those described by Gentile et al. (U.S. Pat. Nos. 5,149,544 and 5,294,544). In addition, inhibition of progenitor cell proliferation can be tested using an in vivo assay. A suitable murine model for assessing progenitor cell proliferation has been described by Cooper et al. (Exp. *Hematol.* 22:186, 1994). The results of this in vivo model, together with the in vitro assay results, are predictive of the efficacy of the tested molecules in treating patients, e.g., humans.

In general, neurotactin proteins according to the invention can be produced by transformation (transfection, transduction, or infection) of a host cell with all or part of a neurotactin-encoding DNA fragment (e.g., the cDNA described herein) in a suitable expression vehicle. Suitable expression vehicles include: plasmids, viral particles, and phage. For insect cells, baculovirus expression vectors are suitable. The entire expression vehicle, or a part thereof, can be integrated into the host cell genome. In some circumstances, it is desirable to employ an inducible expression vector, e.g., the LACSWITCH™ Inducible Expression System (Stratagene, LaJolla, Calif.).

Those skilled in the field of molecular biology will understand that any of a wide variety of expression systems can be used to provide the recombinant protein. The precise host cell used is not critical to the invention. The neurotactin protein can be produced in a prokaryotic host (e.g., *E. coli* or *B. subtilis*) or in a eukaryotic host (e.g., Saccharomyces or Pichia; mammalian cells, e.g., COS, NIH 3T3, CHO, BHK, 293, or HeLa cells; or insect cells).

Proteins and polypeptides can also be produced by plant cells. For plant cells viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.; also, see, e.g., Ausubel et al., *Current Protocols in Molecular Biology,* John Wiley & Sons, New York, 1994). The methods of transformation or transfection and the choice of expression vehicle will depend on the host system selected. Transformation and transfection methods are described, e.g., in Ausubel et al. (*Current Protocols in Molecular Biology,* John Wiley & Sons, New York, 1994); expression vehicles may be chosen from those provided, e.g., in Cloning Vectors: *A Laboratory Manual* (P. H. Pouwels et al., 1985, Supp. 1987).

The host cells harboring the expression vehicle can be cultured in conventional nutrient media adapted as need for activation of a chosen gene, repression of a chosen gene, selection of transformants, or amplification of a chosen gene.

One preferred expression system is the mouse 3T3 fibroblast host cell transfected with a pMAMneo expression vector (Clontech, Palo Alto, Calif.). pMAMneo provides an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a neurotactin protein would be inserted into the pMAMneo vector in an orientation designed to allow expression. The recombinant neurotactin protein would be isolated as described below. Other preferable host cells that can be used in conjunction with the pMAMneo expression vehicle include COS cells and CHO cells (ATCC Accession Nos. CRL 1650 and CCL 61, respectively).

Neurotactin polypeptides can be produced as fusion proteins. For example, the expression vector pUR278 (Ruther et al., *EMBO J.* 2:1791, 1983), can be used to create lacZ fusion proteins. The pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect cell expression system, *Autographa californica* nuclear polyhidrosis virus (AcNPV), which grows in *Spodoptera frugiperda* cells, is used as a vector to express foreign genes. A neurotactin coding sequence can be cloned individually into non-essential regions (for example the polyhedrin gene) of the virus and placed under control of an AcNPV promoter, e.g., the polyhedrin promoter. Successful insertion of a gene encoding a neurotactin polypeptide or protein will result in inactivation of the polyhedrin gene and production of non-occluded recombinant virus (i.e., virus lacking the proteinaceous coat encoded by the polyhedrin gene). These recombinant viruses are then used to infect spodoptera frugiperda cells in which the inserted gene is expressed (see, e.g., Smith et al., *J. Virol.* 46:584, 1983; Smith, U.S. Pat. No. 4,215,051).

In mammalian host cells, a number of viral-based expression systems can be utilized. In cases where an adenovirus is used as an expression vector, the neurotactin nucleic acid sequence can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing a neurotactin gene product in infected hosts (see, e.g., Logan, *Proc. Natl. Acad. Sci. USA* 81:3655, 1984)

Specific initiation signals may also be required for efficient translation of inserted nucleic acid sequences. These signals include the ATG initiation codon and adjacent sequences. In cases where an entire native neurotactin gene or cDNA, including its own initiation codon and adjacent sequences, is inserted into the appropriate expression vector, no additional translational control signals may be needed. In other cases, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators (Bittner et al., *Methods in Enzymol.* 153:516, 1987).

In addition, a host cell may be chosen which modulates the expression of the inserted sequences, or modifies and processes the gene product in a specific, desired fashion. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, WI38, and in particular, choroid plexus cell lines.

Alternatively, a neurotactin protein can be produced by a stably-transfected mammalian cell line. A number of vectors suitable for stable transfection of mammalian cells are available to the public, see, e.g., Pouwels et al. (supra); methods for constructing such cell lines are also publicly available, e.g., in Ausubel et al. (supra). In one example, cDNA encoding the neurotactin protein is cloned into an expression vector that includes the dihydrofolate reductase (DHFR) gene. Integration of the plasmid and, therefore, the neurotactin protein-encoding gene into the host cell chromosome is selected for by including 0.01–300 $\mu$M methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR cells, ATCC Accession No. CRL 9096) are among the host cells preferred for DHFR selection of a stably-transfected cell line or DHFR-mediated gene amplification.

A number of other selection systems can be used, including but not limited to the herpes simplex virus thymidine kinase, hypoxanthine-guanine phosphoribosyltransferase, and adenine phosphoribosyltransferase genes can be employed in tk, hgprt, or aprt cells, respectively. In addition, gpt, which confers resistance to mycophenolic acid (Mulligan et al., *Proc. Natl. Acad. Sci. USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al., *Gene* 30:147, 1981), can be used.

Alternatively, any fusion protein can be readily purified by utilizing an antibody specific for the fusion protein being expressed. For example, a system described in Janknecht et al., *Proc. Natl. Acad. Sci. USA,* 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers.

Alternatively, neurotactin or a portion thereof, can be fused to an immunoglobulin Fc domain. Such a fusion protein can be readily purified using a protein A column. Moreover, such fusion proteins permit the production of a dimeric form of a neurotactin polypeptide having increased stability in vivo.

Neurotactin proteins and polypeptides can also be expressed in transgenic animals. Animals of any species, including, but not limited to, mice, rats, rabbits, guinea pigs, pigs, micro-pigs, goats, and non-human primates, e.g., baboons, monkeys, and chimpanzees, can be used to generate neurotactin-expressing transgenic animals.

Any technique known in the art can be used to introduce a neurotactin transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA* 82:6148, 1985); gene targeting into embryonic stem cells (Thompson et al., *Cell* 56:313, 1989); and electroporation of embryos (Lo, *Mol. Cell. Biol.* 3:1803, 1983).

The present invention provides for transgenic animals that carry the neurotactin transgene in all their cells, as well as animals that carry the transgene in some, but not all of their cells, i.e., mosaic animals. The transgene can be integrated as a single transgene or in concatamers, e.g., head-to-head tandems or head-to-tail tandems. The transgene can also be selectively introduced into and activated in a particular cell type (Lasko et al., *Proc. Natl. Acad. Sci. USA* 89:6232, 1992). The regulatory sequences required for such a cell-type specific activation will depend upon the particular cell type of interest, and will be apparent to those of skill in the art.

When it is desired that the neurotactin transgene be integrated into the chromosomal site of the endogenous neurotactin gene, gene targeting is preferred. Briefly, when such a technique is to be used, vectors containing some nucleotide sequences homologous to an endogenous neurotactin gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous neurotactin gene in only that cell type (Gu et al., Science 265:103, 1984). The regulatory sequences required for such a cell-type specific inactivation will depend upon the particular cell type of interest, and will be apparent to those of skill in the art.

Once transgenic animals have been generated, the expression of the recombinant neurotactin gene can be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of neurotactin gene-expressing tissue, also can be evaluated immunocytochemically using antibodies specific for the neurotactin transgene product.

Once the recombinant neurotactin protein is expressed, it is isolated. Secreted forms can be isolated from the culture media, while non-secreted forms must be isolated from the host cells. Proteins can be isolated by affinity chromatography. In one example, an anti-neurotactin protein antibody (e.g., produced as described herein) is attached to a column and used to isolate the neurotactin protein. Lysis and fractionation of neurotactin protein-harboring cells prior to affinity chromatography can be performed by standard methods (see, e.g., Ausubel et al., supra). Alternatively, a neurotactin fusion protein, for example, a neurotactin-maltose binding protein, a neurotactin-β-galactosidase, or a neurotactin-trpE fusion protein, can be constructed and used for neurotactin protein isolation (see, e.g., Ausubel et al., supra; New England Biolabs, Beverly, Mass.).

Once isolated, the recombinant protein can, if desired, be further purified, e.g., by high performance liquid chromatography using standard techniques (see, e.g., Fisher, *Laboratory Techniques In Biochemistry And Molecular Biology,* eds., Work and Burdon, Elsevier, 1980).

Polypeptides of the invention, particularly short neurotactin fragments, can also be produced by chemical synthesis (e.g., by the methods described in *Solid Phase Peptide Synthesis,* 2nd ed., 1984 The Pierce Chemical Co., Rockford, Ill.).

These general techniques of polypeptide expression and purification can also be used to produce and isolate useful neurotactin fragments or analogs (described herein).

The invention also features proteins which interact with neurotactin and are involved in the function of neurotactin. Also included in the invention are the genes encoding these interacting proteins. Interacting proteins can be identified using methods known to those skilled in the art. One suitable method is the "two-hybrid system," detects protein interactions in vivo (Chien et al., *Proc. Natl. Acad. Sci. USA* 88:9578, 1991). A kit for practicing this method is available from Clontech (Palo Alto, Calif.).

Anti-Neurotactin Antibodies

Human neurotactin proteins and polypeptides (or immunogenic fragments or analogs) can be used to raise antibodies useful in the invention; such polypeptides can be produced by recombinant or peptide synthetic techniques (see, e.g., *Solid Phase Peptide Synthesis,* supra; Ausubel et al., supra). In general, the peptides can be coupled to a carrier protein, such as KLH, as described in Ausubel et al., supra, mixed with an adjuvant, and injected into a host mammal. Antibodies can be purified by peptide antigen affinity chromatography.

In particular, various host animals can be immunized by injection with a neurotactin protein or polypeptide. Host animals include rabbits, mice, guinea pigs, and rats. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.* Polyclonal antibodies are heterogeneous populations of antibody molecules derived from the sera of the immunized animals.

Antibodies within the invention include monoclonal antibodies, polyclonal antibodies, humanized or chimeric antibodies, single chain antibodies, Fab fragments, $F(ab')_2$ fragments, and molecules produced using a Fab expression library.

Monoclonal antibodies, which are homogeneous populations of antibodies to a particular antigen, can be prepared using the neurotactin proteins described above and standard hybridoma technology (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., *In Monoclonal Antibodies and T Cell Hybridomas,* Elsevier, N.Y., 1981; Ausubel et al., supra).

In particular, monoclonal antibodies can be obtained by any technique that provides for the production of antibody molecules by continuous cell lines in culture such as described in Kohler et al., *Nature* 256:495, 1975, and U.S. Pat. No. 4,376,110; the human B-cell hybridoma technique (Kosbor et al., *Immunology Today* 4:72, 1983; Cole et al., *Proc. Natl. Acad. Sci. USA* 80:2026, 1983), and the EBV-hybridoma technique (Cole et al., *Monoclonal Antibodies and Cancer Therapy,* Alan R. Liss, Inc., pp. 77–96, 1983). Such antibodies can be of any immunoglobulin class including IgG, IgM, IgE, IgA, IgD and any subclass thereof. The hybridoma producing the mAb of this invention may be cultivated in vitro or in vivo. The ability to produce high titers of mAbs in vivo makes this the presently preferred method of production.

Once produced, polyclonal or monoclonal antibodies are tested for specific neurotactin recognition by Western blot or immunoprecipitation analysis by standard methods, e.g., as described in Ausubel et al., supra. Antibodies that specifically recognize and bind to neurotactin are useful in the invention. For example, such antibodies can be used in an immunoassay to monitor the level of neurotactin produced by a mammal (for example, to determine the amount or subcellular location of neurotactin).

Preferably, antibodies of the invention are produced using fragments of the neurotactin protein which lie outside highly conserved regions and appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

In some cases it may be desirable to minimize the potential problems of low affinity or specificity of antisera.

In such circumstances, two or three fusions can be generated for each protein, and each fusion can be injected into at least two rabbits. Antisera can be raised by injections in a series, preferably including at least three booster injections.

Antisera is also checked for its ability to immunoprecipitate recombinant neurotactin proteins or control proteins, such as glucocorticoid receptor, CAT, or luciferase.

The antibodies can be used, for example, in the detection of the neurotactin in a biological sample as part of a diagnostic assay. Antibodies also can be used in a screening assay to measure the effect of a candidate compound on expression or localization of neurotactin. Additionally, such antibodies can be used in conjunction with the gene therapy techniques described to, for example, evaluate the normal and/or engineered neurotactin-expressing cells prior to their introduction into the patient. Such antibodies additionally can be used in a method for inhibiting abnormal neurotactin activity.

In addition, techniques developed for the production of "chimeric antibodies" (Morrison et al., *Proc. Natl. Acad. Sci. USA* 81:6851, 1984; Neuberger et al., *Nature* 312:604, 1984; Takeda et al., *Nature* 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; and U.S. Pat. Nos. 4,946,778 and 4,704,692) can be adapted to produce single chain antibodies against a neurotactin protein or polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., *Science* 246:1275, 1989) to allow rapid and easy identification of monoclonal Fab fragments with the desired specificity.

Antibodies to the neurotactin can, in turn, be used to generate anti-idiotype antibodies that resemble a portion of neurotactin using techniques well known to those skilled in the art (see, e.g., Greenspan et al., *FASEB J.* 7:437, 1993; Nissinoff, *J. Immunol.* 147:2429, 1991). For example, antibodies that bind to neurotactin and competitively inhibit the binding of a ligand of neurotactin can be used to generate anti-idiotypes that resemble a ligand binding domain of neurotactin and, therefore, bind and neutralize a ligand of neurotactin. Such neutralizing anti-idiotypic antibodies or Fab fragments of such anti-idiotypic antibodies can be used in therapeutic regimens.

Reducing Neurotactin Expression

In alternate embodiments, anti-inflammation therapy can be designed to reduce the level of endogenous neurotactin gene expression, e.g., using antisense or ribozyme approaches to inhibit or prevent translation of neurotactin mRNA transcripts; triple helix approaches to inhibit transcription of the neurotactin gene; or targeted homologous recombination to inactivate or "knock out" the neurotactin gene or its endogenous promoter. Because the neurotactin gene is expressed in the brain, including the choroid plexus and arcuate nucleus, delivery techniques should be preferably designed to cross the blood-brain barrier (see, e.g., PCT WO89/10134). Alternatively, the antisense, ribozyme, or DNA constructs described herein could be administered directly to the site containing the target cells; e.g., brain, heart, kidney, lung, uterus, endothelial cells, fibroblasts, and bone marrow stromal cells.

Antisense Nucleic Acids

Antisense approaches involve the design of oligonucleotides (either DNA or RNA) that are complementary to neurotactin mRNA. The antisense oligonucleotides bind to the complementary neurotactin mRNA transcripts and prevent translation. Absolute complementarity, although preferred, is not required. A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs recently have been shown to be effective at inhibiting translation of mRNAs as well (Wagner, *Nature* 372:333, 1984). Thus, oligonucleotides complementary to either the 5'- or 3'-non-translated, non-coding regions of the neurotactin gene, e.g., the human gene shown in FIGS. 2A–2B, could be used in an antisense approach to inhibit translation of endogenous neurotactin mRNA. Oligonucleotides complementary to the 5' untranslated region of the mRNA should include the complement of the AUG start codon.

Antisense oligonucleotides complementary to mRNA coding regions are less efficient inhibitors of translation but could be used in accordance with the invention. Whether designed to hybridize to the 5'-, 3'-, or coding region of neurotactin mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (as described, e.g., in Letsinger et al., Proc. Natl. Acad. Sci. USA 86:6553, 1989; Lemaitre et al., Proc. Natl. Acad. Sci. USA 84:648, 1987; PCT Publication No. WO 88/09810) or the blood-brain barrier (see, e.g., PCT Publication No. WO 89/10134), or hybridization-triggered cleavage agents (see, e.g., Krol et al., BioTechniques 6:958, 1988), or intercalating agents (see, e.g., Zon, Pharm. Res. 5:539, 1988). To this end, the oligonucleotide can be conjugated to another molecule, e.g., a peptide, hybridization triggered cross-linking agent, transport agent, or hybridization-triggered cleavage agent.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., Nucl. Acids. Res. 15:6625, 1987). The oligonucleotide is a 2'-0-methylribonucleotide (Inoue et al., Nucl. Acids Res. 15:6131, 1987), or a chimeric RNA-DNA analog (Inoue et al., FEBS Lett. 215:327, 1987).

Antisense oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (Nucl. Acids Res. 16:3209, 1988), and methylphosphonate oligonucleotides can be prepared by use of controlled pore glass polymer supports (Sarin et al., Proc. Natl. Acad. Sci. USA 85:7448, 1988).

While antisense nucleotides complementary to the neurotactin coding region sequence could be used, those complementary to the transcribed untranslated region are most preferred.

One example of a 15 nucleotide antisense sequence to the human neurotactin gene is 5'-TATCGGAGCCATGGC-3' (SEQ ID NO:5), where the underlined sequence represents the complement of the initiator methionine codon.

The antisense molecules should be delivered to cells that express neurotactin in vivo, e.g., brain, heart, kidney, lung, uterus, endothelial cells, fibroblasts, and bone marrow stromal cells. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense molecule sufficient to suppress translation of endogenous mRNAs. Therefore, a preferred approach uses a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous neurotactin transcripts and thereby prevent translation of the neurotactin mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include, but are not limited to: the SV40 early promoter region (Bernoist et al., Nature 290:304, 1981); the promoter contained in the 3' long terminal repeat of Rous sarcoma virus (Yamamoto et al., Cell 22:787–797, 1988); the herpes thymidine kinase promoter (Wagner et al., Proc. Natl. Acad. Sci. USA 78:1441, 1981); or the regulatory sequences of the metallothionein gene (Brinster et al., Nature 296:39, 1988).

Any type of plasmid, cosmid, YAC, or viral vector can be used to prepare the recombinant DNA construct which can be introduced directly into the tissue site; e.g., the brain, heart, kidney, lung, uterus, endothelial cells, fibroblasts, and bone marrow stromal cells. Alternatively, viral vectors can be used that selectively infect the desired tissue (e.g., for brain, herpesvirus vectors may be used), in which case administration can be accomplished by another route (e.g., systemically).

Ribozymes

Ribozyme molecules designed to catalytically cleave neurotactin mRNA transcripts also can be used to prevent translation of neurotactin mRNA and expression of neurotactin (see, e.g., PCT Publication WO 90/11364; Saraver et al., Science 247:1222, 1990). While various ribozymes that cleave mRNA at site-specific recognition sequences can be used to destroy neurotactin mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art (Haseloff et al., Nature 334:585, 1988). There are numerous examples of potential hammerhead ribozyme cleavage sites within the nucleotide sequence of human neurotactin cDNA (FIGS. 2A–2B). Preferably, the ribozyme is engineered so that the cleavage recognition site is located near the 5' end of the neurotactin mRNA, i.e., to increase efficiency and minimize the intracellular accumulation of non-functional mRNA transcripts.

Examples of potential ribozyme sites in human neurotactin include 5'-UG-3' sites which corrspond to the initiator methionine codon (nucleotides 87–88) and the codons for each of the cysteine residues of the chemokine-like domain (e.g., nucleotides 179-180, 191-192, 257-258, and 305-306).

The ribozymes of the present invention also include RNA endoribonucleases (hereinafter "Cech-type ribozymes"), such as the one that occurs naturally in Tetrahymena Thermophila (known as the IVS or L-19 IVS RNA), and which has been extensively described by Cech and his collaborators (Zaug et al., Science 224:574, 1984; Zaug et al., Science 231:470, 1986; Zug et al., Nature 324:429, 1986; PCT Application No. WO 88/04300; and Been et al., Cell 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in neurotactin.

As in the antisense approach, the ribozymes can be composed of modified oligonucleotides (e.g., for improved stability, targeting, etc.), and should be delivered to cells which express the neurotactin in vivo, e.g., brain, heart, kidney, lung, uterus, endothelial cells, fibroblasts, and bone marrow stromal cells. A preferred method of delivery involves using a DNA construct "encoding" the ribozyme under the control of a strong constitutive pol III or pol II promoter, so that transfected cells will produce sufficient quantities of the ribozyme to destroy endogenous neurotactin messages and inhibit translation. Because ribozymes, unlike antisense molecules, are catalytic, a lower intracellular concentration is required for efficiency.

Other Methods for Reducing Neurotactin Expression

Endogenous neurotactin gene expression can also be reduced by inactivating or "knocking out" the neurotactin gene or its promoter using targeted homologous recombination (see, e.g., U.S. Pat. No. 5,464,764). For example, a mutant, non-functional neurotactin (or a completely unrelated DNA sequence) flanked by DNA homologous to the endogenous neurotactin gene (either the coding regions or regulatory regions of the neurotactin gene) can be used, with or without a selectable marker and/or a negative selectable marker, to transfect cells that express neurotactin in vivo. Insertion of the DNA construct, via targeted homologous recombination, results in inactivation of the neurotactin gene. Such approaches are particularly suited for use in the agricultural field where modifications to ES (embryonic stem) cells can be used to generate animal offspring with an inactive neurotactin. However, this approach can be adapted for use in humans, provided the recombinant DNA constructs are directly administered or targeted to the required site in vivo using appropriate viral vectors, e.g., herpes virus vectors for delivery to brain tissue; e.g., the arcuate nucleus or the choroid plexus.

Alternatively, endogenous neurotactin gene expression can be reduced by targeting deoxyribonucleotide sequences complementary to the regulatory region of the neurotactin gene (i.e., the neurotactin promoter and/or enhancers) to form triple helical structures that prevent transcription of the neurotactin gene in target cells in the body (Helene, Anticancer Drug Des. 6:569, 1981; Helene et al., Ann. N.Y. Accad. Sci. 660:27, 1992; and Maher, Bioassays 14:807, 1992).

The Identification of Proteins which Interact with Neurotactin

The invention also features proteins which interact with neurotactin. Any method suitable for detecting protein—protein interactions may be employed for identifying transmembrane proteins, intracellular, or extracellular proteins that interact with neurotactin. Among the traditional methods which may be employed are co-immunoprecipitation, crosslinking and co-purification through gradients or chromatographic columns of cell lysates or proteins obtained from cell lysates and the use of neurotactin to identify proteins in the lysate that interact with the neurotactin. For these assays, the neurotactin polypeptide can be a full length neurotactin, a soluble extracellular domain of neurotactin, or some other suitable neurotactin polypeptide. Once isolated, such an interacting protein can be identified and cloned and then used, in conjunction with standard techniques, to identify proteins with which it interacts. For example, at least a portion of the amino acid sequence of a protein which interacts with the neurotactin can be ascertained using techniques well known to those of skill in the art, such as via the Edman degradation technique. The amino acid sequence obtained may be used as a guide for the generation of oligonucleotide mixtures that can be used to screen for gene sequences encoding the interacting protein. Screening may be accomplished, for example, by standard hybridization or PCR techniques. Techniques for the generation of oligonucleotide mixtures and the screening are well-known. (Ausubel, supra; and PCR Protocols: A Guide to Methods and Applications, 1990, Innis et al., eds. Academic Press, Inc., New York, N.Y.).

Additionally, methods may be employed which result directly in the identification of genes which encode proteins which interact with neurotactin. These methods include, for example, screening expression libraries, in a manner similar to the well known technique of antibody probing of λgt11 libraries, using labeled neurotactin polypeptide or a neurotactin fusion protein, e.g., an neurotactin polypeptide or domain fused to a marker such as an enzyme, fluorescent dye, a luminescent protein, or to an IgFc domain.

In a related aspect, the invention features a method of identifying a compound that modulates the expression or activity of neurotactin. The method is carried out by assessing the expression or activity of neurotactin in the presence and absence of the potential modulatory compound.

Methods which can be used to detect protein interaction are known to those of skill in the art. For example, one method which detects protein interactions in vivo is the two-hybrid system (Chien et al., Proc. Natl. Acad. Sci. USA 88:9578, 1991). A kit for practicing this method is available from Clontech (Palo Alto, Calif.).

Briefly, utilizing such a system, plasmids are constructed that encode two hybrid proteins: one plasmid includes a nucleotide sequence encoding the DNA-binding domain of a transcription activator protein fused to a nucleotide sequence encoding neurotactin, a neurotactin polypeptide, or a neurotactin fusion protein, and the other plasmid includes a nucleotide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, neurotactin may be used as the bait gene product. Total genomic or cDNA sequences are fused to the DNA encoding an activation domain. This library and a plasmid encoding a hybrid of bait neurotactin gene product fused to the DNA-binding domain are cotransformed into a yeast reporter strain, and the resulting transformants are screened for those that express the reporter gene. For example, a bait neurotactin gene sequence, such as neurotactin or a domain of neurotactin can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait neurotactin gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait neurotactin gene-GAL4 fusion plasmid into a yeast strain which contains a lacZ gene driven by a promoter which contains GAL4 activation sequence. A cDNA encoded protein, fused to GAL4 transcriptional activation domain, that interacts with bait neurotactin gene product will reconstitute an active GAL4 protein and thereby drive expression of the HIS3 gene. Colonies which express HIS3 can then be purified from these strains, and used to produce and isolate the bait neurotactin gene-interacting protein using techniques routinely practiced in the art.

Neurotactin and the Treatment of Inflammation

Because neurotactin is highly expressed in the brain, is up-regulated in response to inflammatory stimuli (e.g., LPS and PMA) in endothelial cells (e.g., cells which line the vasculature) and is chemotactic for neutrophils (described in detail below), neurotactin may play a significant role in brain inflammation. Accumulation of neutrophils in tissues is a hallmark of inflammation. Accordingly, undesirable inflammation of the brain associated with disorders such as viral encephalitis, multiple sclerosis, viral or bacterial meningitis, severe head trauma, stroke, neuro-degenerative diseases (e.g., Alzheimer's disease and Lou Gehrig's disease), HIV encephalopathy, primary brain tumors (e.g., glioblastomas), Lupus associated cerebritis, and post-seizure brain injury, can be reduced by the administration of a compound that interferes with neurotactin expression or function.

Compounds which interfere with neurotactin function or expression can also be used to treat other undesirable inflammatory processes, e.g., atherosclerosis or respiratory infections.

Of course, in some circumstances, including certain phases of many of the above-described conditions, it may be desirable to enhance neurotactin function or expression, e.g., to recruit immune cells that will resolve the primary infection or mediate an anti-tumor response.

Neurotactin as a Chemoprotective Agent

This is invention also relates to the use of neurotactin polypeptides to protect myeloid cells, e.g., myeloid progenitor cells, and myeloid stem cells, from drugs or therapies which kill or injure actively dividing cells. Agents which protect myeloid progenitor cells and stem cells in this manner are referred to as chemoprotective agents. Such agents place myeloid progenitor cells (e.g., stem cells) into a protected, slow cell-cycling state, thereby inhibiting or decreasing cell damage or death that could otherwise be caused by cell-cycle active chemotherapy drugs such as cytosine arabinoside, 5-fluorouracil, or hydroxyurea. The use of chemoprotective agents permits the administration of higher doses of chemotherapeutics (or radiation) without compromising the ability of the patient to generate mature functional blood cells.

Many patients who undergo chemotherapy or radiation therapy lose a substantial number of stem cells and other actively dividing myeloid progenitor cells. This loss causes the patients to become susceptible to infection and anemia. One approach for preventing neutropenia is to inhibit cell proliferation with low doses of a molecule which inhibits cell cycling, thereby protecting the progenitor cells from the effects of chemotherapy and/or radiation therapy. After chemotherapy has ended, the protective treatment is also stopped, which allows the progenitor cells to resume normal proliferation.

Any convenient in vitro or in vivo assay can be used to identify preferred neurotactin polypeptides or variants thereof which inhibit progenitor cell proliferation and are thus likely to be a suitable chemoprotective agent.

Suitable in vitro assays include those described by Gentile et al. (U.S. Pat. Nos. 5,149,544 and 5,294,544). In these assays, bone marrow or spleen cells are stimulated with, e.g., CSF, in an in vitro system. The inhibitory activity of a candidate molecule (e.g., neurotactin) is assessed by determining the extent to which it decreases CSF-stimulated colony and cluster formation.

For example, a neurotactin polypeptide or variant can be tested as follows. LD cells are plated at a density of $5 \times 10^5$ cells in 0.3% agar culture medium with 10% FBS (Hyclone, Logan, Utah) for assessment of CFU-GM. CFU-GM colonies (>40 cells/group) are stimulated by human rGM-CSF (100 U/ml) in combination with human rSLF (50 ng/ml). All colonies are tested in the absence or presence of different concentrations of a neurotactin polypeptide (or variant thereof) to determine the degree inhibition of proliferation.

Colonies are scored after 14 days incubation at lowered (5%) $O_2$ tension, and 5% $CO_2$ in a humidified environment in an ESPEC $N_2$—$O_2$—$CO_2$ incubator BNP-210 (Taoi ESPEC Corp., South Plainfield, N.J.). Three plates are scored per determination.

Suitable molecules are those which are effective to significantly inhibit colony formation by human bone marrow GM progenitor cells at concentrations of at least 200 ng/ml, preferably 100 ng/ml, more preferably 50 ng/ml, or even 10 ng/ml. By assaying a number of neurotactin polypeptides it is possible to identify a domain of neurotactin which causes significant inhibition of proliferation.

In addition, inhibition of progenitor cell proliferation can be tested using an in vivo assay. A suitable murine model for assessing progenitor cell proliferation has been described by Cooper et al. (*Exp. Hematol.* 22:186, 1994). The results of this in vivo model, together with the in vitro assay results, are predictive of the efficacy of the tested molecules in treating patients, e.g., humans.

In suitable in vivo tests, molecules are evaluated for effects on myelopoiesis in mice, with endpoints being nucleated cellularity and differentials in the bone marrow, spleen, and peripheral blood, and absolute numbers and cycling status of myeloid progenitor cells in the marrow and spleen. In each test, groups of C3H/HeJ mice are exposed to a particular test sample. C3H/HeJ mice are preferred because they are relatively insensitive to the effects of endotoxin. Thus, any potential endotoxin contamination in the test samples will not influence the in vivo results.

Neurotactin polypeptides can be tested as follows, although other assays are also useful. C3H/HeJ mice are obtained from the Jackson Laboratory (Bar Harbor, Me.) and housed in a conventional animal facility. The mice are injected intravenously with 0.2 ml/mouse sterile pyrogen-free saline, or the stated amount of a selected neurotactin polypeptide or variant as described in Mantel et al. (*Proc. Natl Acad. Sci. USA* 90:2232, 1993). The mice are sacrificed 24 hours later.

The cycling status of hematopoietic progenitor cells, i.e., the proportion of progenitor cells in DNA synthesis (S phase of the cell cycle), is estimated as described in Maze et al. (*J. Immunol.* 149:1004, 1992) and Cooper et al. (*Exp. Hematol.* 22:186, 1994). The high specific activity (20 Ci/mM)-tritiated thymidine (50 $\mu$Ci/mL) (New England Nuclear; Boston, Mass.) kill technique is used, and is based on a calculation in vitro of the reduction in the number of colonies formed after pulse exposure of cells for 20 minutes to "hot" tritiated thymidine as compared with a control such as McCoy's medium or a comparable amount of non-radioactive "cold" thymidine.

Femoral bone marrow is removed from the sacrificed mice, treated with high-specific-activity tritiated thymidine, and plated in 0.3% agar culture medium with 10% FBS in the presence of 10% volume/volume pokeweed mitogen mouse spleen cell cultured medium. Colonies (>40 cells/aggregate) and clusters (3–40 cells) are scored after 7 days of incubation.

Three plates are scored for each sample for a statistical analysis. Each mouse is evaluated separately in groups of three mice each.

Preferred neurotactin polypeptides and variants are effective at a dosage of 200 $\mu$g/mouse, 100 $\mu$g/mouse, 50 $\mu$g/mouse, or even 10 $\mu$g/mouse or lower. An effective dosage will reduce progenitor cell cycling by at least 25% or at least 50% or even more.

Chemoprotective neurotactin polypeptides can be administered to a patient as adjunctive agents before and/or during chemotherapy or radiation therapy to protect progenitor cells from the cytotoxic effects of the chemotherapeutic agents or radiation. Chemoprotective neurotactin polypeptides place myeloid cells into a protected, slow-cycling state, thereby inhibiting or decreasing cell damage that could otherwise be caused by cell-cycle active chemotherapy drugs such as cytosine arabinoside, 5-fluorouracil, or hydroxyurea. The use of chemoprotective agents permits the administration of higher doses of chemotherapeutics without compromising the ability of the patient to generate mature functional blood cells.

Chemoprotective neurotactin polypeptides are administered to a patient in the same manner as chemokines generally, e.g., injected intravenously or subcutaneously, in a pharmaceutically acceptable carrier.

In chemotherapy, specific protocols may vary, and factors such as tumor size, growth rate, and location of the tumor all affect the course of therapy. Administration of chemotherapeutic agents as well as chemoprotective agents require may required knowledge of the extent of disease, the toxicity of previous treatment courses, and the degree of the expected chemotherapeutic drug toxicity.

EXAMPLES

Example 1 describes the identification and sequencing of a murine neurotactin gene and a human neurotactin gene. Example 2 describes the characterization of neurotactin, including its expression pattern and its ability to act as a chemoattractant for neutrophils. Example 3 describes the chromosomal mapping of the neurotactin gene.

Example 1: Cloning of the Neurotactin Gene

The gene for murine neurotactin was identified in a murine choroid plexus cDNA library. This murine neurotactin gene was used to identify a human neurotactin gene. The identification and sequencing of both genes is described in this first example.

Choroid-Plexus mRNA Isolation: The murine mRNA used to create the murine choroid plexus library was prepared as follows. Total RNA was isolated from mouse choroid plexus tissue using the guanidinium isothiocyanate/CsCl method of Chirgwin et al. (*Biochemistry* 18: 5294, 1979) as described in Current Protocols for Molecular Biology (supra). The RNA was quantitated, diluted to 1 mg/ml in water, and then incubated for 30 minutes at 37° C. with an equal volume of DNase solution (20 mM $MgCl_2$, 2 mM DTT, 0.1 units DNase, 0.6 units RNase inhibitor in TE) to remove contaminating DNA. The RNA was then extracted with phenol-chloroform-isoamyl alcohol, and ethanol precipitated. After quantitation at 260 nm, an aliquot was electrophoresed to check the integrity of the RNA. Next, $PolyA^+$ RNA was isolated using an Oligotex-dT kit from Qiagen (Chatsworth, Calif.) as described by the manufacturer. After quantitation, the mRNA was precipitated in ethanol and resuspended at a concentration of 1 mg/ml in water.

cDNA Library Construction: The isolated choroid plexus mRNA described above was used to prepare cDNA as follows.

Choroid plexus mRNA was used as a template for preparation of CDNA according to the method of Gubler et al. (*Gene* 25:263, 1983) using a Superscript Plasmid CDNA synthesis kit (Life Technologies; Gaithersburg, Md.). The cDNA obtained was ligated into the NotI/SalI sites of the mammalian expression vector pMET7, a modified version of pME18S, which utilizes the SRa promoter as described previously (Takebe, *Mol. Cell. Bio.* 8:466, 1988). Ligated cDNA was transformed into electrocompetent DH10B *E. coli* either prepared by standard procedures or obtained from Life Technologies.

DNA Preparation and Sequence Analysis: A number of cDNA clones in the murine choroid plexus library were sequenced to identify sequences of interest. The identified sequences were then used to clone and sequence a complete murine neurotactin gene. The identification and analysis was performed as follows.

First, 96-well plates were inoculated with individual choroid plexus library transformants in 1 ml of LB-amp. These inoculations were based on the titers of the cDNA transformants. The resulting cultures were grown for 15 to 16 hours at 37° C. with aeration. Prior to DNA preparation, 100 µl of cell suspension was removed and added to 100 µl of 50% glycerol, mixed and stored at −80° C. (glycerol freeze plate). DNA was then prepared using the Wizard™ miniprep system (Promega; Madison, Wis.) employing modifications for a 96-well format.

The insert cDNAs of a number of clones were sequenced by standard, automated fluorescent dideoxynucleotide sequencing using dye-primer chemistry (Applied Biosystems, Inc., Foster City, Calif.) on Applied Biosystems 373 and 377 sequenators (Applied Biosystems). The primer used in this sequencing was proximal to the SRa promoter of the vector and therefore selective for the 5' end of the clones, although other primers with this selectivity can also be used. The short cDNA sequences obtained in this manner were screened as follows.

First, each sequence was checked to determine if it was a bacterial, ribosomal, or mitochondrial contaminant. Such sequences were excluded from the subsequent analysis. Second, sequence artifacts, such as vector and repetitive elements, were masked and/or removed from each sequence. Third, the remaining sequences were searched against a copy of the GenBank nucleotide database using the BLASTN program (BLASTN 1.3MP: Altschul et al., *J. Mol. Bio.* 215:403, 1990). Fourth, the sequences were analyzed against a non-redundant protein database with the BLASTX program (BLASTX 1.3MP: Altschul et al., supra). This protein database is a combination of the Swiss-Prot, PIR, and NCBI GenPept protein databases. The BLASTX program was run using the default BLOSUM-62 substitution matrix with the filter parameter: "xnu+seg". The score cutoff utilized was 75.

Assembly of overlapping clones into contigs was done using the program Sequencher (Gene Codes Corp.; Ann Arbor, Mich.). The assembled contigs were analyzed using the programs in the GCG package (Genetic Computer Group, University Research Park, 575 Science Drive, Madison, Wis. 53711).

The above-described analysis resulted in the identification of a clone (clone ID jfmjd006h11) having an open reading frame of 395 amino acids (FIGS. 1A–1B). The protein encoded by this clone was named neurotactin. The first approximately 21 amino acids in this open reading frame were predicted to be a signal sequence using the method of Von Heijne (*J. Membrane Biol.* 115:195, 1990). The amino-terminal portion of murine neurotactin has significant homology to the known C—C family of chemokines. This portion is 40% identical to mouse monocyte MCP-1 based on a primary sequence alignment of residues 23 to 92 of murine neurotactin with murine MCP-1.

The sequence of the murine neurotactin gene was used to search the DBEST expressed sequence tag (EST) database using the BLASTN program. The clone corresponding to a selected EST was obtained from Genome Systems Inc. and sequenced in full (FIGS. 2A–2B). The sequence of this clone differed from that of the initially identified EST at position 319. Compared to the sequence of the clone, there is a one base pair deletion in the EST sequence which results in a reading frame shift. Because of this deletion, the predicted amino acid sequence of the clone differs from the predicted amino acid sequence corresponding to the EST.

This form of human neurotactin is 42% identical to human MCP-1 based on a primary sequence alignment of residue 23 to 92 of human neurotactin with human MCP-1 (Swiss Prot # 13500). Overall human neurotactin contains 397 amino acids and is 67% identical to the form of murine neurotactin described herein (FIG. 4). Higher than average homology is observed at the chemokine-like region at the N-terminal. The regions having the greatest homology are the transmembrane domain and the cytoplasmic domain.

Example 2: Characterization of Neurotactin

The expression pattern of neurotactin was examined as described below. Also described below is the expression of a recombinant form of soluble murine neurotactin and experiments demonstrating that neurotactin stimulates chemotaxis of neutrophils.

Analysis of Neurotactin Expression: Northern analysis was used to examine neurotactin expression as follows. First, total RNA from the following cell types was extracted with RNAsol when the cells were at 80% confluence: WEH1-3 and Pu5-1.8 (myelomonocytes), P388D1 and IC-21 (macrophages), AKR.G.2 (thymoma), BaF3 (Pro B cell), EL-4 (Lymphoma), NFS-1.0 (B cell lymphoma), BCL (B cell leukemia), STO (embryonic fibroblasts), EOMA (endothelial), and BMS-12 (bone marrow stromal). Except for EOMA cells and BMS-12 cells, all of these cells were maintained according to procedures described by the American Type Culture Collection (Bethesda, Md.). EOMA cells were maintained in DMEM with 10% FCS, and BMS-12 cells were maintained in DMEM with 10% horse serum. In order to determine the effect of activators on neurotactin, cells were treated with 100 ng/ml LPS or 30 ng/ml PMA for 4 hours prior to RNA extraction or were left untreated.

Northern blots containing 20 µg of total RNA were probed using standard techniques (Chirgwin et al., *Biochemistry* 18:5294, 1979) with a $^{32}$P-labeled DNA fragment encoding the full-length neurotactin.

This Northern analysis revealed that a 3.5 kb neurotactin mRNA is constitutively expressed in endothelial cells (EOMA) and embryonic fibroblasts (STO). The 3.5 kb mRNA is upregulated in these cells when they are stimulated with LPS and PMA. This mRNA is also upregulated in bone marrow stromal cells (BMS-12) when treated with LPS and PMA. It is not expressed by unstimulated BMS-12 cells. This expression pattern is characteristic of modulators of inflammation.

Neurotactin mRNA was not detected in several cell lines of hematopoietic origin with or without stimulation by PMA and LPS. The tested cell lines were WEHI-3 and Pu5-1.8 (myelomonocytic), P388D1 and IC-21 (monocytic/macrophage), ARK.G.2 (thymoma), BaF3 (pro B cell), EL-4 (lymphoma), NFS-1.0 (B cell lymphoma) and BCL (B cell leukemia).

This same Northern analysis revealed the presence of messages having the following approximate sizes: 1.5 kb, 4.4 kb, and 5.5 kb. These messages are likely to represent alternatively spliced forms of neurotactin or the transcription products of related genes.

Human tissue Northern blots showed that human neurotactin is highly expressed in the brain and the heart. Furthermore, hybridization to a brain tissue Northern blot (Clontech) showed that the mRNA was expressed in all parts of the brain.

In situ hybridizations were also used to examine neurotactin expression. Tissues for these hybridization were prepared as follows. Four to six week old C57BL/6 mice were anesthetized and perfused with PBS followed by 4% paraformaldehyde (PFA/PBS). The brains were then removed and stored in 10% buffered formalin. Ten $\mu$m coronal frozen sections of brain were post-fixed with 4% PFA/PBS for 15 minutes. After washing with PBS, sections were digested with 2 $\mu$g/ml proteinase K at 370 for 15 minutes, and then incubated with 4% PFA/PBS for 10 minutes. Sections were then washed with PBS, incubated with 0.2 N HCl for 10 minutes, washed with PBS, incubated with 0.25% acetic anhydride/1 M triethanolamine for 10 minutes, washed with PBS, and dehydrated with 70% ethanol and 100% ethanol.

Hybridizations were performed with $^{35}$S-radiolabeled (5×10 cpm/ml) antisense cRNA probes encoding a 1.9 kb segment of the coding region of the murine neurotactin gene (clone 6h11) in the presence of 50% formamide, 10% dextran sulfate, 1× Denhardt's solution, 600 mM NaCl, 10 mM DTT, 0.25% SDS, and 100 $\mu$g/ml tRNA for 18 hours at 55° C. After hybridization, the slides were washed with 5× SSC at 55° C., 50% formamide/2× SSC at 55° C. for 30 minutes, 10 mM Tris-HCl (pH 7.6)/500 mM NaCl/1 mM EDTA(TNE) at 37° C. for 10 minutes, incubated in 10 $\mu$g/ml RNase A in TNE at 37° C. for 30 minutes, washed in TNE at 37° C. for 10 minutes, incubated once in 2× SSC at 50° C. for 30 minutes, twice in 0.2× SSC at 50° C. for 30 minutes, and dehydrated with 70% ethanol and 100% ethanol. Localization of mRNA transcripts was detected by dipping slides in Kodak NBT-2 photoemulsion and exposed for 4 days at 4° C. Controls for the in situ hybridization experiments included the use of a sense probe which showed no signal above background levels.

These in situ hybridizations with murine neurotactin probe showed that neurotactin is expressed in the arcuate nucleus. Expression was also detected in the cortex and choroid plexus.

To determine the association of neurotactin with the cell membrane, a construct containing the full-length neurotactin coding region was made in a mammalian expression vector, pN83. Full-length murine neurotactin cDNA was modified for expression in a mammalian system by PCR with the following primers:
5'-GGGAAAGAATTCATGGCTCCCTCGCCGCTCGCG TCC-3' (SEQ ID NO:6) and
5'-GGGAAACTCGAGTCATTTATCATCATCATCTTT ATAATCCACTGGCACCAGGACGTA
TGA-3' (SEQ ID NO:7). Nucleotides encoding a FLAG epitope tag (DYKDDDDK (SEQ ID NO:8), which can be detected with an M2 anti-FLAG antibody, were incorporated into the 3' "reverse" primer. The PCR products were cloned into the pN83 vector bearing the EBV origin of replication. The construct DNA was prepared with the Qiagen Max-iprep™ kit (Qiagen, Chatsworth, Calif.) and transfected with lipofectamine™ (Gibco, Gaithersburg, Md.) into 293 EBNA cells that were cultured in 8-well chamber slides. Forty-eight hours after transfection, the cells were fixed with 50% methanol and 50% acetone for 1 minute at room temperature, washed four times with 2.5 ml TBS, and incubated with 10 $\mu$g/ml of M2 anti-FLAG monoclonal antibody (Eastman Kodak Co., New Haven, Conn.) and then with FITC-conjugated goat anti-mouse antibody at 1:1000 dilution (Jackson Immuno Research, West Grove, Pa.). The cells were exposed to the primary and secondary antibodies for one hour each. The immunofluorescent staining was visualized under 200-fold magnification. Strong staining was detected on the surface of the transfected 293 EBNA cells, suggesting full-length neurotactin is indeed membrane-anchored. The signal observed could be competed out by adding an excess of the FLAG peptide to the incubation.

Example 3: Preparation of Soluble Neurotactin

A soluble form of recombinant murine neurotactin (residues 22–105) was produced in bacteria using the pGEX expression system. The pGEX-neurotactin was purified on glutathione agarose and the neurotactin moiety released by thrombin digestion. Following endotoxin removal on an Endotoxin BX column (Cape Cod Associates: Falmouth, Mass.) the neurotactin preparation was determined to contain low levels of endotoxin (<0.01 EU/ml) by the Limulus amebocyte lysate (LAL) assay (Cape Cod Associates).

Recombinant, soluble neurotactin was produced as follows. First, the coding region of mouse neurotactin was amplified with a primer corresponding to a sequence at the 5' end of the sequence encoding the chemokine-like domain (5' primer). The 5' primer,
5'-GGGAAAGAATTCCTGCCGGGTCAGCACCTC GGCATG-3' (SEQ ID NO:9),
has an EcoRI restriction enzyme cleavage site followed by 24 nucleotides encoding the beginning of the chemokine-like domain of murine neurotactin. The 3' primer used was 5'-GGGAAACTCGAGTCATTCTCAAACTTGCCACC ATTTTA-3' (SEQ ID NO:10). This primer has complementary sequences encoding amino acids 99 to 105 preceded by a termination codon and XhoI site.

These primers pairs were used for PCR amplification using the following conditions: 94° C. for 30 seconds; 55° C. for 30 seconds and 72° C. for 90 seconds with 30 cycles. The resulting PCR product was cloned into the GST fusion protein vector pGEX-4T (Pharmacia, Piscataway, N.J.). The fusion protein was produced in E. coli and purified according to the protocol supplied by the manufacturer. The neurotactin construct produced a protein of approximately 10,000 kDa after the cleavage of GST by thrombin.

Example 4: Neurotactin acts as a Neutrophil Chemoattractant

The ability of a soluble form of recombinant neurotactin described above was tested for its ability to act as a chemoattractant for neutrophils.

The human neutrophils used in these experiments were isolated by layering 20 ml of human blood over 10 ml of FICOLL 1119 and 10 ml of FICOLL 1077 (Sigma; St Louis, Mo.) in a 50 ml conical polypropylene tube and centrifuging at 1800 rpm for 15 minutes at room temperature. Following centrifugation, the neutrophil layer was washed with sterile, ice cold, calcium and magnesium-free phosphate buffered saline (Gibco; Bethesda, Md.), and the neutrophil pellet was resuspended in 45 ml sterile, cold $H_2O$ and 5 ml sterile 10X phosphate buffered saline (PBS) to lyse contaminating red blood cells. The cells were pelleted by centrifugation at 1800 rpm for 5 minutes at 4° C. The pelleted neutrophils were resuspended in 10 ml of sterile PBS, quantitated, and kept on ice until needed for in vitro assays.

The ability of neurotactin to elicit neutrophil chemotaxis was tested in an in vitro assay as described by Falk et al. (J. Immunol. Meth. 33:39, 1980). Approximately 50,000 neutrophils were added to each well of a 48-well micro chemotaxis chamber containing a 5 $\mu$m pore size filter. Varying concentrations of neurotactin or human interleukin-8 (Biosource International, Camarillo, Calif.) were added to the lower chamber of each appropriate well. The cells were then incubated at 37° C., 5% $CO_2$ for 30 minutes. The upper chamber was removed and the cells on the filter from the upper chamber were removed by scraping. The filter was fixed in 100% ethanol and stained with a solution of 0.5% toluidine blue in 3.7% formaldehyde. Excess stain was removed with distilled water. Migrated cells were quantitated by counting three high power fields (400× magnification) per well. The number of cells that migrated to the buffer control were subtracted as background. The activities of compounds in this assay are predictive of the ability of compounds to elicit neutrophil chemotaxis in vivo.

Figure 5:
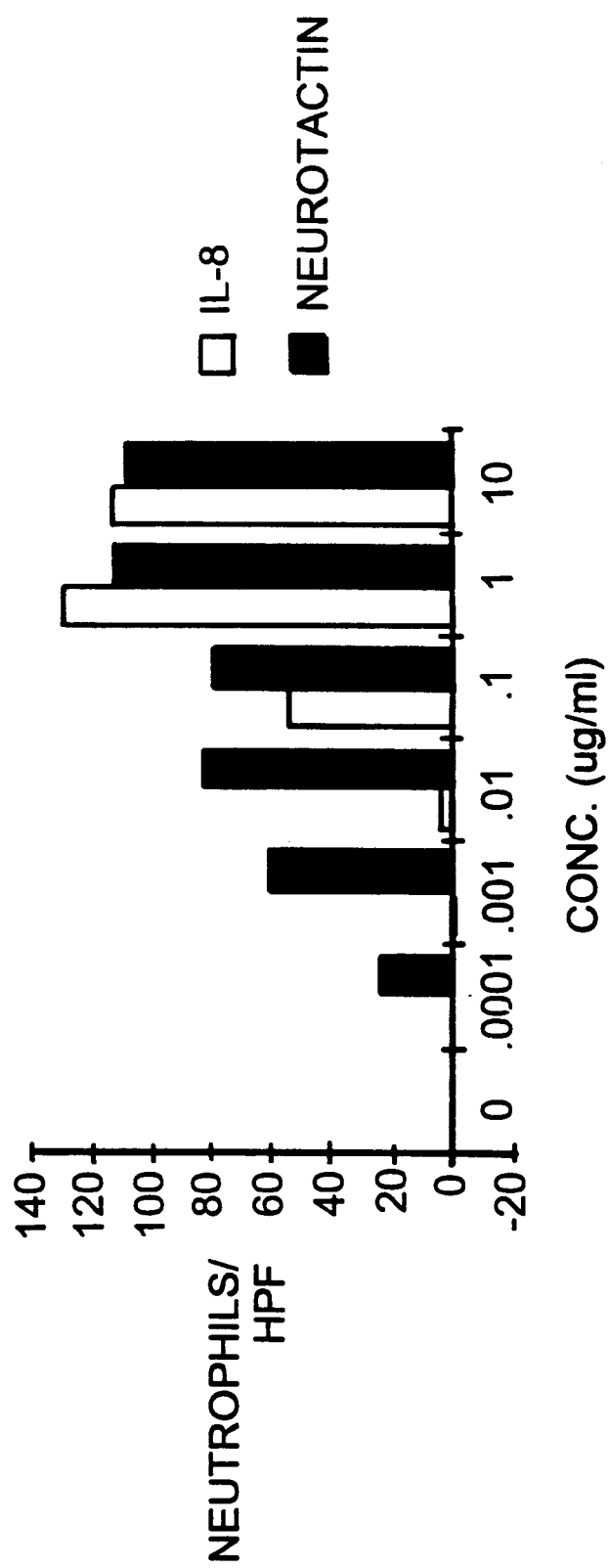
FIG. 5 is a graph illustrating the results of a neutrophil chemotaxis assay.

The results of this assay are presented in FIG. 5. This figure provides a comparison of the ability of human interleukin-8 and neurotactin to elicit neutrophil chemotaxis. As can be seen in the figure, neurotactin is chemotactic for human neutrophils with an approximate endpoint titer (concentration giving 50% of the maximal stimulation level) of 1 ng/ml. This endpoint titer compares favorably with that of human interleukin-8, a known neutrophil chemoattractant.

A soluble version of murine neurotactin, corresponding to the chemokine-like domain (residues 22 to 105), was also chemotactic for human T lymphocytes. Further testing showed that neither this chemokine-like domain nor an entire extracellular domain had a chemotactic effect on human monocytes, human myelomonocytic THP1 cells, or murine P388D1 monocytic cells.

Two soluble versions of murine neurotactin (corresponding to the chemokine-like domain (residues 22 to 105) and the entire extracellular domain (residues 22 to 337)) were also injected into C57BL/6J mice intraperitoneally to determine the chemotactic efficacy in vivo. Bacterial lysate containing only glutathione S-transferase was purified in the same fashion as these soluble forms of neurotactin and served as a control for the in vivo assay. Neurotactin and the control protein were both administered at a dose of 0.5 μg/400 μl PBS/mouse. In addition, some mice received only 400 μl of PBS. Two hours after the injection, peritoneal exudate was collected and the number and subtype of leukocytes recovered in the fluid were determined by typing and counting the cells in four high power fields (40× magnification; total area 0.5 mm$^2$) The neutrophils and eosinophils were identified by staining with Wright-Giemsa, and lymphocytes were assessed by Thy 1.2 (53-2.1) and IgM (II/41) immunostaining.

The chemokine-like domain (residues 22 to 105) was chemotactic for neutrophils and lymphocytes (as predicted from in vitro studies), and was also chemotactic for monocytes. However, the activity of the chemokine-like domain towards monocytes may be due to a secondary effect in vivo and may not, therefore, reflect the chemotactic specificity of neurotactin. The chemokine-like domain of neurotactin was not chemotactic for eosinophils. The entire extracellular domain (residues 22 to 337) failed to act as a chemoattractant for monocytes and lymphocytes in vivo but was chemotactic for neutrophils.

Example 5: Neurotactin expression patterns in normal mice, LPS-treated mice, and mice with severe experimental autoimmune encephalomyelitis Experimental autoimmune encephalomyelitis (EAE) is a mouse model of T cell mediated autoimmune disease that shares many clinical and histological features with multiple sclerosis. Central nervous system myelin is the target of an immune attack in multiple sclerosis, but the cellular and molecular mechanisms that lead to myelin breakdown have not been fully elucidated. Two major proteins of CNS myelin that can induce EAE are myelin basic protein (MBP) and proteolipid protein (PLP) (Zamvil and Steinman, *Annual Rev. Immunol* 8:579; 1990). It is generally thought that EAE is a delayed-type hypersensitivity (DTH) reaction. Although myelin antigen-specific Th1 cells are required to initiate the disease, most of the cells in the EAE lesions are non-specifically recruited. The infiltrating cells consist primarily of T cells and macrophages and, to a lesser extent, B cells. In some cases, polymorphs are also detected in EAE lesions (Sobel et al., *J. Neuropathol. Exp. Neurol.* 49:468, 1989). It is likely that the infiltrating cells play a major role in the tissue damage. Activated macrophages have been demonstrated to strip axons of myelin. In addition, activated macrophages secrete numerous cytokines, including IL-1 and TNF-α, nitric oxide, free oxygen radicals, and proteolytic enzymes, all of which can further perpetuate non-specific inflammatory reactions and contribute to tissue damage (Oppenheim and Gery, *Immunol. Today* 3:113, 1982; Scheurich et al., *J. Immunol.* 138:1786, 1987). Moreover, activated T cells produce proinflammatory chemotactic cytokines (chemokines), which play an important role in the non-specific recruitment of inflammatory cells (Oppenheim et al., *Annu. Rev. Immunol.* 9:617, 1991).

EAE can be induced by immunizing susceptible strains of mice with either proteins found in myelin (e.g., MBP or PLP) or with their peptides (Milner et al., *Cell* 42:931, 1985; Kuchroo et al., *J. Immunol.* 151:4371, 1985).

In addition, EAE develops spontaneously in immunodeficient α-myelin basic protein T cell receptor transgenic mice, which are used as a model of chronic inflammatory diseases.

Neurotactin expression in the brain was determined by immunohistochemistry in mice with severe experimental autoimmune encephalomyelitis (EAE), normal mice, and mice treated with LPS using a polyclonal anti-neurotactin antibody.

For these experiments, polyclonal anti-neurotactin antibody was raised in rabbits against a peptide located at the amino terminus of neurotactin (LPGQHLGMTKCEIM; SEQ ID NO:11); Research Genetics, Huntsville, Ala.). The antibody was affinity purified from 12-week bleeds. For LPS treatment, 8 week old CD1 mice were injected intravenously with 40 μg LPS and sacrificed 2 hours later by cervical dislocation. Their brains were removed, bisected transversely, and coated with Tissue Tek™ OCT compound (Cryoform). The OCT-coated tissue was then snap frozen in a mixture of isopentane and dry ice and stored at −70° C. Sections (3 μm thick) were cut onto microscope slides, air dried, fixed in 2% paraformaldehyde (for 5 minutes at 4° C.) and methanol (10 minutes at −20° C.). To study neurotactin expression in the EAE model, brains were collected from male α-myelin basic protein T cell receptor (MBP TCR) transgenic mice (at about 4 months of age) and fixed in 10% neutral buffered formalin and embedded in paraffin. Sections (4 μm) were microwaved twice for 5 minutes in 0.01 M sodium citrate (pH 6.0) before staining.

The fixed sections were stained with antibody using an avidin/biotin staining method. All incubations were carried out under humidified conditions and slides were washed twice between the steps for 5 minutes each in 0.1 M phosphate buffered saline supplemented with 0.2% gelatin (PBSG). The sections were overlaid with 20% fetal calf serum in PBS for 15 minutes and then incubated overnight at 4° C. with polyclonal anti-neurotactin or normal rabbit serum (both diluted to 1:200 in PBS supplemented with 0.1% bovine serum albumin). Endogenous peroxide was blocked by incubation for 20 minutes in methanol containing 0.3% hydrogen peroxide. Non-specific staining due to cross reaction with endogenous avidin or biotin was blocked by incubation with avidin solution followed by biotin solution, both for 20 minutes. Bound monoclonal antibody was visualized by incubation with biotinylated swine antirabbit immunoglobulin (Dako, Calif.) and then streptavidin peroxidase complex, both diluted in 10% normal mouse serum with PBS, and incubated for one hour. The slides were then flooded with peroxidase substrate solution (400 µg diaminobenzidine in 10 ml PBS containing 0.01% hydrogen peroxide) for 10 minutes. The sections were counterstained with haematoxylin. Control sections were generated by selectively omitting monoclonal antibody, biotinylated anti-rat immunoglobulin or streptavidin complex. In addition, competitive inhibition of the antibody was accomplished by preincubation of antibody with the peptide (25 µg/ml) for 45 minutes at 37° C. prior to incubation with the tissue sections.

In the normal mouse brain, staining was localized to capillary vessels and resident microglia. An increased intensity of labeling was observed on the same cell types two hours after LPS treatment. In addition, an increased number of activated microglial cells stained positive for the anti-neurotactin antibody. In both normal and LPS-treated brain, staining of larger vessels was restricted to the apical region of the endothelium. It is known that, in addition to resident microglial cells, two other subtypes of microglial cell are present in the CNS at the blood-brain barrier: perivascular and juxtavascular microglia. The anti-neurotactin antibody staining associated with micro vessels was consistent with the staining of those microglial cells. Neurotactin expression was also up-regulated in activated microglial in the brains of EAE mice.

Example 6: Mapping of the Neurotactin Gene

Described in this example is the chromosome mapping of neurotactin. Also described below is the potential relationship between neurotactin and Bardet-Biedl Syndrome.

Mouse Chromosome Mapping: The following PCR primers were used to amplify mouse genomic DNA.

Forward primer: 5'-CACAGTCCACCCCTCAG-3' (SEQ ID NO:12)

Reverse primer, 5'-GCTCTGGTAAGCAAACATGG-3' (SEQ ID NO:13).

PCR reactions were performed on genomic DNA from a panel of interspecific backcrossed mice. The amplification profile was as follows: 94° C. (30 seconds); 55° C. (30 seconds); and 72° C. (45 seconds) with 30 cycles. Samples were run on nondenaturing 10% acrylamide SSCP gel at 20 W and 4° C. for 2.5 hours.

Murine neurotactin was mapped to the long arm of mouse chromosome 8, between D8MIT35 and D8MIT74, by using a panel of backcrossed progeny of the C57Bl/6J and *Mus spretus*. The region is syntenic to human chromosome 16.

Human Chromosome Mapping: Human neurotactin was mapped to chromosome 16q, between W17078 and WI6174, using a panel of radiation hybrids.

The following primers were used to amplify human genomic DNA from a panel of radiation hybrids (Genebridge 4, Research Genetics, Huntsville, Ala.).

Forward: 5'-TGTGAACTCCTCTGGCCTGT-3' (SEQ ID NO:14)

Reverse: 5'-GAAGGGGCTGGGCATTTAAT-3' (SEQ ID NO:15)

The amplification profile was as follows: 94° C. for 30 seconds; 55° C. for 30 seconds, and 72° C. for 45 seconds with 30 cycles. Samples were resolved on 1% agarose TAE gel.

Based on a published article (Kwitek-Black et al., *Nature Genetics* 5:392, 1993) and the integrated genetic map of Chromosome 16 (Genome Directory, *Nature* 377:335, 1995), the region to which neurotactin gene maps overlaps with a locus for the a gene important in Bardet-Biedl Syndrome (BBS).

BBS is a heterogeneous autosomal recessive disorder characterized by obesity, mental retardation, polydactyly, retinitis pigmentosa and hypogonadism. Patients suffering from this syndrome have a high incident of renal and cardiovascular abnormalities. The fact that neurotactin is expressed in tissues and organs which may be affected in BBS suggests that neurotactin may play a role in BBS. For example, BBS is characterized by obesity and mental retardation, and neurotactin is expressed in the arcuate nucleus, a region of the brain thought to play a role in weight control, and other parts of the brain. BBS is also associated with renal and cardiovascular symptoms, and neurotactin is expressed in the kidney and heart. In addition, BBS is associated with hypogonadism, and neurotactin is expressed in the uterus.

Example 7: Anti-Neurotactin antibodies slow progression of experimental autoimmune encephalomyelitis The experiments described in this section demonstrate that anti-neurotactin antibodies can slow the progression of EAE in mice.

Generation of anti-neurotactin antibodies: A fusion protein consisting of the entire extracellular domain of murine neurotactin (amino acids L22 to R387) was fused to GST was prepared as follows. DNA encoding the extracellular domain of murine neurotactin was constructed by PCR using modified oligonucleotides and Taq polymerase (Stratagene; La Jolla, Calif.). The forward primer was 5'-GGGAAAGAATTCCTGCCGGGTCAGCACCTC GGCATG-3' (SEQ ID NO:16) and the reverse primer was 5'-GGGAAACTCGAGTCACCTTGTGGCTGCCTG GGTGTCGGG-3' (SEQ ID NO:17). The PCR products were ligated to EcoRI/XhoI digested pGEX-4T (Pharmacia; Piscataway, N.J.) and the ligation products were used to transform *E. coli* DH5a (Life Technology; Gaithersburg, Md.). A clone encoding the desired soluble neurotactin fragment fused in frame to GST was identified. This clone was used to express the fusion protein which was purified with glutathione-sepharose according to the manufacturer's instructions. Polyclonal anti-neurotactin antibody was raised in rabbits (Research Genetics) and the antibody was purified from serum by protein A chromatography.

In this experiment EAE mice were generated as follows. Female SJL mice (12 weeks of age) were immunized with 40 µg PLP peptide 139-151 (Prabhu et al., *J. Exp. Med.* 186:867, 1997) (HSLGKWLGHPDKF; SEQ ID NO:18) in complete Freund's adjuvant (CFA). Pertussis toxin (400 ng/mouse) was also administered intravenously. Anti-neurotactin antibody was administered (30 µg/mouse) every other day. The disease course was followed for about a month. The control mice received 0.2 ml PBS every other day intravenously. The disease is scored as follows: 1=limp tail (tail atony); 2=hind limb weakness, no righting ability; 3=hind limb paralysis and incontinence; 4=all four limbs are paralyzed; and 5=moribund.

Figure 6:
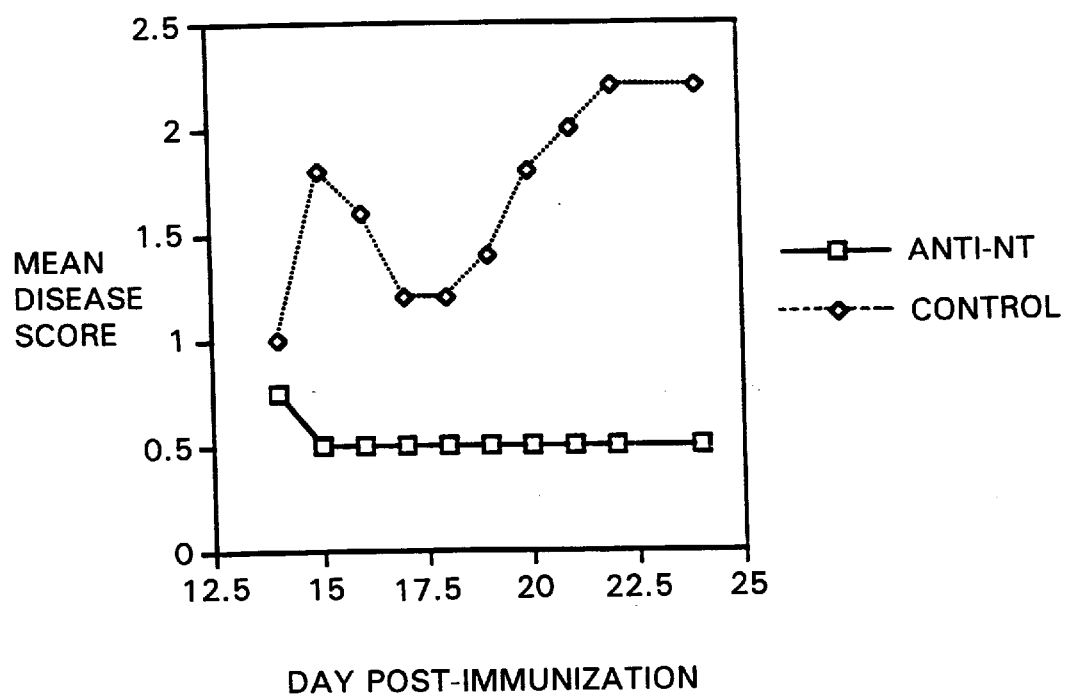
FIG. 6 is a graph demonstrating that an anti-neurotactin antibody can slow the progression of experimental autoimmune encephalomyelitis.

The results of this study are summarized in FIG. 6, which shows that the mean disease score for mice treated with anti-neurotactin antibody (open squares) is considerably lower than the mean disease score for untreated mice (open diamonds).

Therapeutic Applications

The neurotactin proteins and polypeptides described herein stimulate chemotaxis of neutrophils and lymphocytes. Accordingly, neurotactin proteins and polypeptides are likely to mediate inflammation. Consistent with this expectation is the fact that anti-neurotactin antibody slows the progression of EAE significantly. This suggests that anti-neurotactin antibodies and other inhibitors of neurotactin expression or activity can be used to treat other inflammatory disorders. Accordingly, undesirable inflammation of the brain associated with disorders such as viral encephalitis, multiple sclerosis, viral or bacterial meningitis, severe head trauma, stroke, neuro-degenerative diseases (e.g., Alzheimer's disease and Lou Gehrig's disease), HIV encephalopathy, primary brain tumors (e.g., glioblastomas), Lupus associated cerebritis, and post-seizure brain injury, can be reduced by the administration of a compound that interferes with neurotactin expression or function (e.g., an antibody). Compounds which interfere with neurotactin function may also be used to treat other undesirable inflammatory processes, e.g., atherosclerosis or respiratory infections.

Neurotactin, like other chemokines (Lord et al., *Blood* 85:3412, 1995; Laterveer et al., *Blood* 85:2269, 1995), can be used to mobilize hematopoietic stem cells and progenitor cells from the bone marrow to the peripheral blood. Because stem cells and progenitor cells can be more easily recovered from the peripheral blood than from bone marrow, neurotactin may be useful for isolating such cells for use in stem cell restorative therapy. Such therapy is useful for patients which have undergone myeloablative and/or myelosuppresive cancer treatments.

Neurotactin is likely to be involved in the regulation of hematopoietic cells. In particular, neurotactin, like other chemokines (Graham et al., *Nature* 344:442, 1994; Broxmeyer et al., *J. Immunol.* 150:3448, 1993), may be able to inhibit proliferation of hematopoietic stem cells and progenitor cells. Such inhibition can protect the cells from chemotherapeutic damage. Thus, neurotactin can be used to protect hematopoietic stem cells and progenitor cells from chemotherapeutic damage, e.g, damage during chemotherapy for cancer.

The neurotactin polypeptides which inhibit progenitor cell proliferation can be used to inhibit hyperproliferative myeloid based diseases such as chronic myelogenous leukemia, polycythemia vera, and hypermegakaryocytopoietic disorders. Hyperproliferative states in such disorders occur because the progenitor cells are unable to negatively regulate cell growth and replication. Administration of suitable neurotactin polypeptides is expected to inhibit cell replication resulting in the inhibition of the abnormal cell growth. Dosages of the neurotactin polypeptides for treating hyperproliferative myeloid based diseases would be similar to those dosages described above for use of the proteins as adjuncts to chemotherapy.

In addition, neurotactin polypeptides can be used to prevent myeloid progenitor cells from becoming leukemic as the result of the administration of chemotherapeutic agents. The neurotactin polypeptides are administered in the same way described above.

Recombinant neurotactin may facilitate the production of pharmacologic modifiers of neurotactin function. Such therapeutic polypeptides of the invention can be administered by any appropriate route, e.g., intravenously, at a dosage that is effective to modulate neurotactin function. Treatment may be repeated as necessary for alleviation of disease symptoms.

Diagnostic Applications

The nucleic acids, polypeptides, and antibodies of the invention are useful for identifying those compartments of mammalian cells which contain proteins important to the function of neurotactin. Antibodies specific for neurotactin may be produced as described above. The normal subcellular location of the protein is then determined either in situ or using fractionated cells by any standard immunological or immunohistochemical procedure (see, e.g., Ausubel et al., supra; Bancroft and Stevens, *Theory and Practice of Histological Techniques,* Churchill Livingstone, 1982).

Antibodies specific for neurotactin also find diagnostic use in the detection or monitoring of neurotactin-related diseases. Levels of a neurotactin protein in a sample can be assayed by any standard technique. For example, neurotactin protein expression can be monitored by standard immunological or immunohistochemical procedures (e.g., those described above) using the antibodies described herein. Alternatively, neurotactin expression can be assayed by standard Northern blot analysis or can be aided by PCR (see, e.g., Ausubel et al., supra; *PCR Technology: Principles and Applications for DNA Amplification,* ed., H. A. Ehrlich, Stockton Press, NY). If desired or necessary, analysis can be carried out to detect point mutations in the neurotactin sequence (for example, using well known nucleic acid mismatch detection techniques). All of the above techniques are enabled by the neurotactin sequences described herein.

Accordingly, the nucleic acids, polypeptides and antibodies of the invention can be used in a method for determined whether a patient has a disorder associated with abnormal expression of neurotactin. The method can be carried out by quantitating the level of expression of neurotactin in a biological sample obtained from the patient. As a control, the quantitation can be carried out using a biological sample obtained from a patient who is healthy.

Neurotactin expression can be assessed at the level of gene expression, for example, by quantitating the level of neurotactin mRNA expression in the biological sample, or at the level of protein expression, by quantitating the level of neurotactin protein expressed. Quantitation can be carried out using the techniques described above, which are well within the abilities of those of skill in the art to perform.

Should it be determined that a patient has a disorder that is associated with abnormal expression or activity of neurotactin, the patient can be given a compound that modulates that expression or activity. For example, the patient can receive a compound such as a small molecule, an antisense nucleic acid molecule, or a ribozyme, that inhibits the expression of neurotactin. The patient can also receive a compound that inhibits the activity of neurotactin. An antibody that specifically binds neurotactin can be used for this purpose. Alternatively, the patient can receive a compound that enhances the expression or activity of neurotactin. Compounds that inhibit or enhance the expression or activity of neurotactin can include synthetic molecules. These methods of treatment can be used to treat inflammatory disorders and disorders associated with cellular proliferation, as described more fully above.

Other Embodiments

The invention also features fragments, variants, analogs and derivatives of the neurotactin polypeptides described above that retain one or more of the biological activities of neurotactin such as neutrophil chemotaxis.

The invention includes naturally-occurring and non-naturally-occurring allelic variants. Compared to the most common naturally-occurring nucleotide sequence encoding neurotactin, the nucleic acid sequence encoding allelic variants may have a substitution, deletion, or addition of one or more nucleotides. The preferred allelic variants are functionally equivalent to naturally-occurring neurotactin.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

---

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 1784 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 40...1224

(xi) SEQUENCE DESCRIPTION: SEQ ID NO:1:

```
GTCGACCCAC GCGTCCGGCC GAATTCCTGC ACTCCAGCC ATG GCT CCC TCG CCG          54
                                           Met Ala Pro Ser Pro
                                            1               5

CTC GCG TGG CTG CTG CGC CTG GCC GCG TTC TTC CAT TTG TGT ACT CTG        102
Leu Ala Trp Leu Leu Arg Leu Ala Ala Phe Phe His Leu Cys Thr Leu
            10                  15                  20

CTG CCG GGT CAG CAC CTC GGC ATG ACG AAA TGC GAA ATC ATG TGC GAC        150
Leu Pro Gly Gln His Leu Gly Met Thr Lys Cys Glu Ile Met Cys Asp
                25                  30                  35

AAG ATG ACC TCA CGA ATC CCA GTG GCT TTG CTC ATC CGC TAT CAG CTA        198
Lys Met Thr Ser Arg Ile Pro Val Ala Leu Leu Ile Arg Tyr Gln Leu
            40                  45                  50

AAC CAG GAG TCC TGC GGC AAG CGT GCC ATT GTC CTG GAG ACG ACA CAG        246
Asn Gln Glu Ser Cys Gly Lys Arg Ala Ile Val Leu Glu Thr Thr Gln
        55                  60                  65

CAC AGA CGC TTC TGT GCT GAC CCG AAG GAG AAA TGG GTC CAA GAC GCC        294
His Arg Arg Phe Cys Ala Asp Pro Lys Glu Lys Trp Val Gln Asp Ala
 70                 75                  80                  85

ATG AAG CAT CTG GAT CAC CAG GCT GCT GCC CTC ACT AAA AAT GGT GGC        342
Met Lys His Leu Asp His Gln Ala Ala Ala Leu Thr Lys Asn Gly Gly
                90                  95                 100

AAG TTT GAG AAG CGG GTG GAC AAT GTG ACA CCT GGG ATC ACC TTG GCC        390
Lys Phe Glu Lys Arg Val Asp Asn Val Thr Pro Gly Ile Thr Leu Ala
                105                 110                 115

ACT AGG GGA CTG TCC CCA TCT GCC CTG ACA AAG CCT GAA TCC GCC ACA        438
Thr Arg Gly Leu Ser Pro Ser Ala Leu Thr Lys Pro Glu Ser Ala Thr
            120                 125                 130

TTG GAA GAC CTT GCT TTG GAA CTG ACT ACT ATT TCC CAG GAG GCC AGG        486
Leu Glu Asp Leu Ala Leu Glu Leu Thr Thr Ile Ser Gln Glu Ala Arg
        135                 140                 145

GGG ACC ATG GGG ACT TCC CAA GAG CCA CCG GCA GCA GTG ACC GGA TCA        534
Gly Thr Met Gly Thr Ser Gln Glu Pro Pro Ala Ala Val Thr Gly Ser
150                 155                 160                 165

TCT CTC TCA ACT TCC GAG GCA CAG GAT GCA GGG CTT ACG GCT AAG CCT        582
Ser Leu Ser Thr Ser Glu Ala Gln Asp Ala Gly Leu Thr Ala Lys Pro
                170                 175                 180

CAG AGC ATT GGA AGT TTT GAG GCG GCT GAC ATC TCC ACC ACC GTT TGG        630
Gln Ser Ile Gly Ser Phe Glu Ala Ala Asp Ile Ser Thr Thr Val Trp
            185                 190                 195

CCG AGT CCT GCT GTC TAC CAA TCT GGA TCT AGC TCC TGG GCT GAG GAA        678
```

```
                Pro Ser Pro Ala Val Tyr Gln Ser Gly Ser Ser Ser Trp Ala Glu Glu
                                200                 205                 210

AAA GCT ACT GAG TCC CCC TCC ACT ACA GCC CCA TCT CCT CAG GTG TCC              726
Lys Ala Thr Glu Ser Pro Ser Thr Thr Ala Pro Ser Pro Gln Val Ser
        215                 220                 225

ACT ACT TCA CCT TCA ACC CCA GAG GAA AAT GTT GGG TCC GAA GGC CAA              774
Thr Thr Ser Pro Ser Thr Pro Glu Glu Asn Val Gly Ser Glu Gly Gln
230                 235                 240                 245

CCC CCA TGG GTC CAG GGA CAG GAC CTC AGT CCA GAG AAG TCT CTA GGG              822
Pro Pro Trp Val Gln Gly Gln Asp Leu Ser Pro Glu Lys Ser Leu Gly
                250                 255                 260

TCT GAG GAG ATA AAC CCA GTT CAT ACT GAT AAT TTC CAG GAG AGG GGG              870
Ser Glu Glu Ile Asn Pro Val His Thr Asp Asn Phe Gln Glu Arg Gly
            265                 270                 275

CCT GGC AAC ACA GTC CAC CCC TCA GTG GCT CCC ATC TCC TCT GAA GAG              918
Pro Gly Asn Thr Val His Pro Ser Val Ala Pro Ile Ser Ser Glu Glu
        280                 285                 290

ACC CCC AGC CCA GAG CTG GTG GCC TCG GGC AGC CAG GCT CCT AAG ATA              966
Thr Pro Ser Pro Glu Leu Val Ala Ser Gly Ser Gln Ala Pro Lys Ile
295                 300                 305

GAG GAA CCC ATC CAT GCC ACT GCA GAT CCC CAG AAA CTG AGT GTG CTT             1014
Glu Glu Pro Ile His Ala Thr Ala Asp Pro Gln Lys Leu Ser Val Leu
310                 315                 320                 325

ATC ACT CCT GTC CCC GAC ACC CAG GCA GCC ACA AGG AGG CAG GCA GTG             1062
Ile Thr Pro Val Pro Asp Thr Gln Ala Ala Thr Arg Arg Gln Ala Val
                330                 335                 340

GGG CTA CTG GCT TTC CTT GGT CTT CTT TTC TGC CTA GGG GTG GCC ATG             1110
Gly Leu Leu Ala Phe Leu Gly Leu Leu Phe Cys Leu Gly Val Ala Met
            345                 350                 355

TTT GCT TAC CAG AGC CTT CAG GGC TGT CCC CGC AAA ATG GCG GGG GAA             1158
Phe Ala Tyr Gln Ser Leu Gln Gly Cys Pro Arg Lys Met Ala Gly Glu
        360                 365                 370

ATG GTA GAA GGC CTC CGC TAC GTC CCC CGT AGC TGT GGC AGT AAC TCA             1206
Met Val Glu Gly Leu Arg Tyr Val Pro Arg Ser Cys Gly Ser Asn Ser
375                 380                 385

TAC GTC CTG GTG CCA GTG TGAGCTGCTT GCCTGCCTGC CTGTGTCCAG AGTGTGAT           1262
Tyr Val Leu Val Pro Val
390                 395

TCGGACAGCT GTCTGGGGAC CCCCCCCCAT CCTCATACCC ACCTTCATCC ACGCTGGGGA           1322

AATGGGAATG GAGAAGCTGG ACCCTCCAGG GGCTGTGGGC TCCATCCAAT CCCCCCTCCC           1382

CCGAGGGGTG GCCCCGGAGG CCACCCTAGA CCACTATTCA CTTATCAGAG ACAGAGCAGG           1442

TGACCTTCCA GCTCCTCTAT ATTTGAAAGA ATCCTCTGCT GCTGGCTGGT TAGAGGGGCC           1502

CTTGACACCC CAACTCCAGT GAACAATTAT TTATTGGATT CCCAGCCCCT GCGACGACAC           1562

CTGTTTCCCG CGCGCACCGT GGTCCGCCCA TATCACAAGC AGCAGGCCAG GCCTATCTGC           1622

CTGTCCCCCT GACCTCCTTG TGTCTCCTGG CTTTGCTGCA GTCGCCAGCC CTTCTCCTCC           1682

CCGGCCAGCT GCGGTGCTAT CTGCCCTATG TCTCCCTCTA TCCCCTGTAC AGAGCGCACC           1742

ACCATCACCA TCAAAAAAAA AAAAAAAAAA AAGGGCGGCC GC                             1784

(2) INFORMATION FOR SEQ ID NO:2:

(i) SEQUENCE CHARACTERISTICS:
        (A) LENGTH: 395 amino acids
        (B) TYPE: amino acid
        (D) TOPOLOGY: linear (ii) MOLECULE TYPE: protein (v) FRAGMENT TYPE: internal
```

(xi) SEQUENCE DESCRIPTION: SEQ ID NO:2:

```
Met Ala Pro Ser Pro Leu Ala Trp Leu Leu Arg Leu Ala Ala Phe Phe
 1               5                  10                  15
His Leu Cys Thr Leu Leu Pro Gly Gln His Leu Gly Met Thr Lys Cys
             20                  25                  30
Glu Ile Met Cys Asp Lys Met Thr Ser Arg Ile Pro Val Ala Leu Leu
         35                  40                  45
Ile Arg Tyr Gln Leu Asn Gln Glu Ser Cys Gly Lys Arg Ala Ile Val
     50                  55                  60
Leu Glu Thr Thr Gln His Arg Arg Phe Cys Ala Asp Pro Lys Glu Lys
 65                  70                  75                  80
Trp Val Gln Asp Ala Met Lys His Leu Asp His Gln Ala Ala Ala Leu
                 85                  90                  95
Thr Lys Asn Gly Gly Lys Phe Glu Lys Arg Val Asp Asn Val Thr Pro
            100                 105                 110
Gly Ile Thr Leu Ala Thr Arg Gly Leu Ser Pro Ser Ala Leu Thr Lys
        115                 120                 125
Pro Glu Ser Ala Thr Leu Glu Asp Leu Ala Leu Glu Leu Thr Thr Ile
    130                 135                 140
Ser Gln Glu Ala Arg Gly Thr Met Gly Thr Ser Gln Glu Pro Pro Ala
145                 150                 155                 160
Ala Val Thr Gly Ser Ser Leu Ser Thr Ser Glu Ala Gln Asp Ala Gly
                165                 170                 175
Leu Thr Ala Lys Pro Gln Ser Ile Gly Ser Phe Glu Ala Ala Asp Ile
            180                 185                 190
Ser Thr Thr Val Trp Pro Ser Pro Ala Val Tyr Gln Ser Gly Ser Ser
        195                 200                 205
Ser Trp Ala Glu Glu Lys Ala Thr Glu Ser Pro Ser Thr Thr Ala Pro
    210                 215                 220
Ser Pro Gln Val Ser Thr Thr Ser Pro Ser Thr Pro Glu Glu Asn Val
225                 230                 235                 240
Gly Ser Glu Gly Gln Pro Pro Trp Val Gln Gly Gln Asp Leu Ser Pro
                245                 250                 255
Glu Lys Ser Leu Gly Ser Glu Glu Ile Asn Pro Val His Thr Asp Asn
            260                 265                 270
Phe Gln Glu Arg Gly Pro Gly Asn Thr Val His Pro Ser Val Ala Pro
        275                 280                 285
Ile Ser Ser Glu Glu Thr Pro Ser Pro Glu Leu Val Ala Ser Gly Ser
    290                 295                 300
Gln Ala Pro Lys Ile Glu Glu Pro Ile His Ala Thr Ala Asp Pro Gln
305                 310                 315                 320
Lys Leu Ser Val Leu Ile Thr Pro Val Pro Asp Thr Gln Ala Ala Thr
                325                 330                 335
Arg Arg Gln Ala Val Gly Leu Leu Ala Phe Leu Gly Leu Leu Phe Cys
            340                 345                 350
Leu Gly Val Ala Met Phe Ala Tyr Gln Ser Leu Gln Gly Cys Pro Arg
        355                 360                 365
Lys Met Ala Gly Glu Met Val Glu Gly Leu Arg Tyr Val Pro Arg Ser
    370                 375                 380
Cys Gly Ser Asn Ser Tyr Val Leu Val Pro Val
385                 390                 395
```

(2) INFORMATION FOR SEQ ID NO:3:

(i) SEQUENCE CHARACTERISTICS:
    (A) LENGTH: 1654 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: Coding Sequence
    (B) LOCATION: 86...1276

(xi) SEQUENCE DESCRIPTION: SEQ ID NO:3:

```
AAGCTTGGCA CGAGGGCACT GAGCTCTGCC GCCTGGCTCT AGCCGCCTGC CTGGCCCCCG        60

CCGGGACTCT TGCCCACCCT CAGCC ATG GCT CCG ATA TCT CTG TCG TGG CTG        112
                            Met Ala Pro Ile Ser Leu Ser Trp Leu
                             1               5

CTC CGC TTG GCC ACC TTC TGC CAT CTG ACT GTC CTG CTG GCT GGA CAG        160
Leu Arg Leu Ala Thr Phe Cys His Leu Thr Val Leu Leu Ala Gly Gln
 10              15                  20                  25

CAC CAC GGT GTG ACG AAA TGC AAC ATC ACG TGC AGC AAG ATG ACA TCA        208
His His Gly Val Thr Lys Cys Asn Ile Thr Cys Ser Lys Met Thr Ser
                 30                  35                  40

AAG ATA CCT GTA GCT TTG CTC ATC CAC TAT CAA CAG AAC CAG GCA TCA        256
Lys Ile Pro Val Ala Leu Leu Ile His Tyr Gln Gln Asn Gln Ala Ser
             45                  50                  55

TGC GGC AAA CGC GCA ATC ATC TTG GAG ACG AGA CAG CAC AGG CTG TTC        304
Cys Gly Lys Arg Ala Ile Ile Leu Glu Thr Arg Gln His Arg Leu Phe
 60                  65                  70

TGT GCC GAC CCG AAG GAG CAA TGG GTC AAG GAC GCG ATG CAG CAT CTG        352
Cys Ala Asp Pro Lys Glu Gln Trp Val Lys Asp Ala Met Gln His Leu
 75                  80                  85

GAC CGC CAG GCT GCT GCC CTA ACT CGA AAT GGC GGC ACC TTC GAG AAG        400
Asp Arg Gln Ala Ala Ala Leu Thr Arg Asn Gly Gly Thr Phe Glu Lys
 90                  95                 100                 105

CAG ATC GGC GAG GTG AAG CCC AGG ACC ACC CCT GCC GCC GGG GGA ATG        448
Gln Ile Gly Glu Val Lys Pro Arg Thr Thr Pro Ala Ala Gly Gly Met
                110                 115                 120

GAC GAG TCT GTG GTC CTG GAG CCC GAA GCC ACA GGC GAA AGC AGT AGC        496
Asp Glu Ser Val Val Leu Glu Pro Glu Ala Thr Gly Glu Ser Ser Ser
                125                 130                 135

CTG GAG CCG ACT CCT TCT TCC CAG GAA GCA CAG AGG GCC CTG GGG ACC        544
Leu Glu Pro Thr Pro Ser Ser Gln Glu Ala Gln Arg Ala Leu Gly Thr
                140                 145                 150

TCC CCA GAG CTG CCG ACG GGC GTG ACT GGT TCC TCA GGG ACC AGG CTC        592
Ser Pro Glu Leu Pro Thr Gly Val Thr Gly Ser Ser Gly Thr Arg Leu
 155                 160                 165

CCC CCG ACG CCA AAG GCT CAG GAT GGA GGG CCT GTG GGC ACG GAG CTT        640
Pro Pro Thr Pro Lys Ala Gln Asp Gly Gly Pro Val Gly Thr Glu Leu
170                 175                 180                 185

TTC CGA GTG CCT CCC GTC TCC ACT GCC GCC ACG TGG CAG AGT TCT GCT        688
Phe Arg Val Pro Pro Val Ser Thr Ala Ala Thr Trp Gln Ser Ser Ala
                190                 195                 200

CCC CAC CAA CCT GGG CCC AGC CTC TGG GCT GAG GCA AAG ACC TCT GAG        736
Pro His Gln Pro Gly Pro Ser Leu Trp Ala Glu Ala Lys Thr Ser Glu
                205                 210                 215

GCC CCG TCC ACC CAG GAC CCC TCC ACC CAG GCC TCC ACT GCG TCC TCC        784
Ala Pro Ser Thr Gln Asp Pro Ser Thr Gln Ala Ser Thr Ala Ser Ser
                220                 225                 230

CCA GCC CCA GAG GAG AAT GCT CCG TCT GAA GGC CAG CGT GTG TGG GGT        832
Pro Ala Pro Glu Glu Asn Ala Pro Ser Glu Gly Gln Arg Val Trp Gly
 235                 240                 245
```

```
CAG GGA CAG AGC CCC AGG CCA GAG AAC TCT CTG GAG CGG GAG GAG ATG       880
Gln Gly Gln Ser Pro Arg Pro Glu Asn Ser Leu Glu Arg Glu Glu Met
250                 255                 260                 265

GGT CCC GTG CCA GCG CAC ACG GAT GCC TTC CAG GAC TGG GGG CCT GGC       928
Gly Pro Val Pro Ala His Thr Asp Ala Phe Gln Asp Trp Gly Pro Gly
                270                 275                 280

AGC ATG GCC CAC GTC TCT GTG GTC CCT GTC TCC TCA GAA GGG ACC CCC       976
Ser Met Ala His Val Ser Val Val Pro Val Ser Ser Glu Gly Thr Pro
            285                 290                 295

AGC AGG GAG CCA GTG GCT TCA GGC AGC TGG ACC CCT AAG GCT GAG GAA      1024
Ser Arg Glu Pro Val Ala Ser Gly Ser Trp Thr Pro Lys Ala Glu Glu
        300                 305                 310

CCC ATC CAT GCC ACC ATG GAC CCC CAG AGG CTG GGC GTC CTT ATC ACT      1072
Pro Ile His Ala Thr Met Asp Pro Gln Arg Leu Gly Val Leu Ile Thr
    315                 320                 325

CCT GTC CCT GAC GCC CAG GCT GCC ACC CGG AGG CAG GCG GTG GGG CTG      1120
Pro Val Pro Asp Ala Gln Ala Ala Thr Arg Arg Gln Ala Val Gly Leu
330                 335                 340                 345

CTG GCC TTC CTT GGC CTC CTC TTC TGC CTG GGG GTG GCC ATG TTC ACC      1168
Leu Ala Phe Leu Gly Leu Leu Phe Cys Leu Gly Val Ala Met Phe Thr
                350                 355                 360

TAC CAG AGC CTC CAG GGC TGC CCT CGA AAG ATG GCA GGA GAG ATG GCG      1216
Tyr Gln Ser Leu Gln Gly Cys Pro Arg Lys Met Ala Gly Glu Met Ala
            365                 370                 375

GAG GGC CTT CGC TAC ATC CCC CGG AGC TGT GGT AGT AAT TCA TAT GTC      1264
Glu Gly Leu Arg Tyr Ile Pro Arg Ser Cys Gly Ser Asn Ser Tyr Val
        380                 385                 390

CTG GTG CCC GTG TGAACTCCTC TGGCCTGTGT CTAGTTGTTT GATTCAGACA GCTGC    1321
Leu Val Pro Val
    395

CTGGGATCCC TCATCCTCAT ACCCACCCCC ACCCAAGGGC CTGGCCTGAG CTGGGATGAT    1381

TGGAGGGGGG AGGTGGGATC CTCCAGGTGC ACAAGCTCCA AGCTCCCAGG CATTCCCCAG    1441

GAGGCCAGCC TTGACCATTC TCCACCTTCC AGGGACAGAG GGGGTGGCCT CCCAACTCAC    1501

CCCAGCCCCA AAACTCTCCT CTGCTGCTGG CTGGTTAGAG GTTCCCTTTG ACGCCATCCC    1561

AGCCCCAATG AACAATTATT TATTAAATGC CCAGCCCCTT CTGAAAAAAA AAAAAAAAA    1621

AAAAAAAAAA AAAAAAAAA TTCCTGCGGC CGC                                  1654

(2) INFORMATION FOR SEQ ID NO:4:

(i) SEQUENCE CHARACTERISTICS:
        (A) LENGTH: 397 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:4:

Met Ala Pro Ile Ser Leu Ser Trp Leu Leu Arg Leu Ala Thr Phe Cys
  1               5                  10                  15

His Leu Thr Val Leu Leu Ala Gly Gln His His Gly Val Thr Lys Cys
                20                  25                  30

Asn Ile Thr Cys Ser Lys Met Thr Ser Lys Ile Pro Val Ala Leu Leu
            35                  40                  45

Ile His Tyr Gln Gln Asn Gln Ala Ser Cys Gly Lys Arg Ala Ile Ile
        50                  55                  60

Leu Glu Thr Arg Gln His Arg Leu Phe Cys Ala Asp Pro Lys Glu Gln
```

```
              65                  70                  75                  80
Trp Val Lys Asp Ala Met Gln His Leu Asp Arg Gln Ala Ala Ala Leu
                        85                  90                  95
Thr Arg Asn Gly Gly Thr Phe Glu Lys Gln Ile Gly Glu Val Lys Pro
            100                 105                 110
Arg Thr Thr Pro Ala Ala Gly Gly Met Asp Glu Ser Val Val Leu Glu
            115                 120                 125
Pro Glu Ala Thr Gly Glu Ser Ser Leu Glu Pro Thr Pro Ser Ser
        130                 135                 140
Gln Glu Ala Gln Arg Ala Leu Gly Thr Ser Pro Glu Leu Pro Thr Gly
145                 150                 155                 160
Val Thr Gly Ser Ser Gly Thr Arg Leu Pro Pro Thr Pro Lys Ala Gln
                165                 170                 175
Asp Gly Gly Pro Val Gly Thr Glu Leu Phe Arg Val Pro Pro Val Ser
            180                 185                 190
Thr Ala Ala Thr Trp Gln Ser Ser Ala Pro His Gln Pro Gly Pro Ser
            195                 200                 205
Leu Trp Ala Glu Ala Lys Thr Ser Glu Ala Pro Ser Thr Gln Asp Pro
        210                 215                 220
Ser Thr Gln Ala Ser Thr Ala Ser Ser Pro Ala Pro Glu Glu Asn Ala
225                 230                 235                 240
Pro Ser Glu Gly Gln Arg Val Trp Gly Gln Gly Ser Pro Arg Pro
                245                 250                 255
Glu Asn Ser Leu Glu Arg Glu Glu Met Gly Pro Val Pro Ala His Thr
            260                 265                 270
Asp Ala Phe Gln Asp Trp Gly Pro Gly Ser Met Ala His Val Ser Val
            275                 280                 285
Val Pro Val Ser Ser Glu Gly Thr Pro Ser Arg Glu Pro Val Ala Ser
        290                 295                 300
Gly Ser Trp Thr Pro Lys Ala Glu Glu Pro Ile His Ala Thr Met Asp
305                 310                 315                 320
Pro Gln Arg Leu Gly Val Leu Ile Thr Pro Val Pro Asp Ala Gln Ala
                325                 330                 335
Ala Thr Arg Arg Gln Ala Val Gly Leu Leu Ala Phe Leu Gly Leu Leu
            340                 345                 350
Phe Cys Leu Gly Val Ala Met Phe Thr Tyr Gln Ser Leu Gln Gly Cys
            355                 360                 365
Pro Arg Lys Met Ala Gly Glu Met Ala Glu Gly Leu Arg Tyr Ile Pro
        370                 375                 380
Arg Ser Cys Gly Ser Asn Ser Tyr Val Leu Val Pro Val
385                 390                 395

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:5:

TATCGGAGCC ATGGC                                                       15

(2) INFORMATION FOR SEQ ID NO:6:

(i) SEQUENCE CHARACTERISTICS:
        (A) LENGTH: 36 base pairs
```

```
            (B) TYPE: nucleic acid
            (C) STRANDEDNESS: single
            (D) TOPOLOGY: linear (xi) SEQUENCE DESCRIPTION: SEQ ID NO:6:

GGGAAAGAAT TCATGGCTCC CTCGCCGCTC GCGTCC                              36

(2) INFORMATION FOR SEQ ID NO:7:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (xi) SEQUENCE DESCRIPTION: SEQ ID NO:7:

GGGAAACTCG AGTCATTTAT CATCATCATC TTTATAATCC ACTGGCACCA GGACGTATGA    60

(2) INFORMATION FOR SEQ ID NO:8:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:8:

Asp Tyr Lys Asp Asp Asp Asp Lys
 1               5

(2) INFORMATION FOR SEQ ID NO:9:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:9:

GGGAAAGAAT TCCTGCCGGG TCAGCACCTC GGCATG                              36

(2) INFORMATION FOR SEQ ID NO:10:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:10:

GGGAAACTCG AGTCATTCTC AAACTTGCCA CCATTTTTA                           39

(2) INFORMATION FOR SEQ ID NO:11:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (xi) SEQUENCE DESCRIPTION: SEQ ID NO:11:

Leu Pro Gly Gln His Leu Gly Met Thr Lys Cys Glu Ile Met
 1               5                  10

(2) INFORMATION FOR SEQ ID NO:12:
```

```
    (i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:12:

CACAGTCCAC CCCTCAG                                                      17

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:13:

GCTCTGGTAA GCAAACATGG                                                   20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:14:

TGTGAACTCC TCTGGCCTGT                                                   20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GAAGGGGCTG GGCATTTAAT                                                   20

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GGGAAAGAAT TCCTGCCGGG TCAGCACCTC GGCATG                                 36

(2) INFORMATION FOR SEQ ID NO:17:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GGGAAACTCG AGTCACCTTG TGGCTGCCTG GGTGTCGGG                              39
```

(2) INFORMATION FOR SEQ ID NO:18:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:18:

```
His Ser Leu Gly Lys Trp Leu Gly His Pro Asp Lys Phe
 1               5                  10
```

I claim:

1. A method for treating a patient suffering from multiple sclerosis comprising administering an antibody which binds to a protein having the amino acid sequence of SEQ ID NO:4.

2. The method of claim 1 wherein said antibody binds to a protein having the amino acid sequence of SEQ ID NO:4 from amino acid 22 to amino acid 341, inclusive.

3. The method of claim 1 wherein said antibody binds to a protein having the amino acid sequence of SEQ ID NO:4 from amino acid 22 to amino acid 92, inclusive.

4. The method of any of claims 1–3 wherein said antibody is a monoclonal antibody.

* * * * *